United States Patent
Makino et al.

(10) Patent No.: US 11,701,032 B2
(45) Date of Patent: *Jul. 18, 2023

(54) ELECTRONIC ENDOSCOPE PROCESSOR AND ELECTRONIC ENDOSCOPIC SYSTEM

(71) Applicant: HOYA CORPORATION, Tokyo (JP)

(72) Inventors: Takao Makino, Tokyo (JP); Yousuke Ikemoto, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,098

(22) Filed: Jun. 7, 2022

(65) Prior Publication Data

US 2022/0296123 A1 Sep. 22, 2022

Related U.S. Application Data

(63) Continuation of application No. 16/308,451, filed as application No. PCT/JP2017/031123 on Aug. 30, 2017, now Pat. No. 11,589,777.

(30) Foreign Application Priority Data

Aug. 31, 2016 (JP) ................. 2016-169231

(51) Int. Cl.
 *A61B 5/103* (2006.01)
 *A61B 1/045* (2006.01)
 (Continued)

(52) U.S. Cl.
 CPC ........ *A61B 5/1032* (2013.01); *A61B 1/00009* (2013.01); *A61B 1/045* (2013.01);
 (Continued)

(58) Field of Classification Search
 CPC ....... A61B 5/1032; A61B 5/00; A61B 5/7425; A61B 1/00009; A61B 1/045; G06T 1/00; G06T 1/60; H04N 7/01

See application file for complete search history.

(56) References Cited

U.S. PATENT DOCUMENTS

2009/0109284 A1 4/2009 Takayama
2013/0051642 A1* 2/2013 Kanda ................. G06T 7/90
 382/128

(Continued)

FOREIGN PATENT DOCUMENTS

CN 104540438 A 4/2015
JP 2009-106424 A 5/2009

(Continued)

OTHER PUBLICATIONS

U.S. Appl. No. 16/308,451, "Notice of Allowance", dated Dec. 13, 2022, 8 pages.

(Continued)

*Primary Examiner* — Sean D Mattson
(74) *Attorney, Agent, or Firm* — Kilpatrick Townsend & Stockton LLP

(57) ABSTRACT

An electronic endoscope processor includes a converting means for converting each piece of pixel data that is made up of n (n≥3) types of color components and constitutes a color image of a biological tissue in a body cavity into a piece of pixel data that is made up of m (m≥2) types of color components, m being smaller than n; an evaluation value calculating means for calculating, for each pixel of the color image, an evaluation value related to a target illness based on the converted pieces of pixel data that are made up of m types of color components; and a lesion index calculating means for calculating a lesion index for each of a plurality of types of lesions related to the target illness based on the evaluation values calculated for the pixels of the color image.

5 Claims, 11 Drawing Sheets

(51) Int. Cl.
  *A61B 5/00* (2006.01)
  *G06T 1/00* (2006.01)
  *G06T 1/60* (2006.01)
  *A61B 1/00* (2006.01)
  *G06V 10/75* (2022.01)
  *H04N 7/18* (2006.01)

(52) U.S. Cl.
  CPC .............. *A61B 5/00* (2013.01); *A61B 5/7425* (2013.01); *G06T 1/00* (2013.01); *G06T 1/60* (2013.01); *G06V 10/751* (2022.01); *H04N 7/18* (2013.01)

(56) References Cited

U.S. PATENT DOCUMENTS

| | | | |
|---|---|---|---|
| 2013/0176411 A1 | 7/2013 | Igarashi et al. | |
| 2014/0320620 A1* | 10/2014 | Ikemoto | G06T 7/90 348/71 |
| 2015/0181185 A1* | 6/2015 | Ikemoto | G06T 7/0012 348/71 |
| 2016/0100789 A1 | 4/2016 | Huang | |
| 2017/0018083 A1 | 1/2017 | Kuramoto | |
| 2019/0192048 A1* | 6/2019 | Makino | A61B 5/00 |

FOREIGN PATENT DOCUMENTS

| | | |
|---|---|---|
| JP | 2012-152284 A | 8/2012 |
| JP | 2014-018333 A | 2/2014 |
| JP | 2014-213094 A | 11/2014 |
| JP | 2016-077756 A | 5/2016 |

OTHER PUBLICATIONS

U.S. Appl. No. 16/308,451, "Non-Final Office Action", dated Mar. 10, 2022, 17 pages.

CN201780035272.7, First Office Action dated Sep. 2, 2020, with machine translation, 15 pages.

PCT/JP2017/031123, International Search Report, dated Oct. 10, 2017, 2 pages.

U.S. Appl. No. 16/308,451, "Final Office Action", dated Jul. 5, 2022, 15 pages.

U.S. Appl. No. 16/308,451, "Advisory Action", dated Oct. 26, 2022, 3 pages.

* cited by examiner

ELECTRONIC ENDOSCOPE PROCESSOR AND ELECTRONIC ENDOSCOPIC SYSTEM

CROSS-REFERENCE TO RELATED APPLICATIONS

This application is a continuation of U.S. application Ser. No. 16/308,451, filed Dec. 7, 2018, which is a 371 U.S. National Phase of PCT International Application No. PCT/JP2017/031123, filed on Aug. 30, 2017, which claims benefit and priority to Japanese patent application No. 2016-169231 filed on Aug. 31, 2016, and which are incorporated by reference herein in their entirety.

TECHNICAL FIELD

The present disclosure relates to an electronic endoscope processor and an electronic endoscope system.

BACKGROUND ART

A lesion site generally has a different color from normal mucosal tissue. Through improvements in the capabilities of color endoscope apparatuses, it has also become possible to also identify lesion sites that have a slight difference in color from normal tissue. However, an operator has needed to receive extensive training under an experienced operator in order to be able to accurately distinguish a lesion site from normal tissue based on a slight color difference in an endoscopic image. Also, it is not easy for even an experienced operator to identify a lesion site based on a slight color difference, and such identification has required careful work. In view of this, in order to make the identification of blood vessels and lesion sites easier, there has been a proposal for an electronic endoscope system that includes a function for performing color conversion processing for emphasizing color differences in endoscope image data that was obtained using white light (Patent Document 1).

CITATION LIST

Patent Document

[Patent Document 1] JP 2009-106424A

SUMMARY OF DISCLOSURE

Technical Problem

Images generated by the electronic endoscope system in Patent Document 1 make it possible to more easily identify lesion sites and the like than in normal endoscopic images, but the change in color is continuous at the boundary between normal mucosal tissue and a lesion site or the like, and the difference in color from normal mucosal tissue may be slight depending on the type of illness, and therefore there have been cases where it remains difficult for an inexperienced operator to identify lesion sites or the like. Also, even when using the electronic endoscope system in Patent Document 1, the determination of whether a site is a lesion site or not is ultimately dependent on image-reading skill, which is dependent on the amount of experience and knowledge of the operator, and it has not been possible to obtain examination results that are objective and reproducible (not dependent on the operator's skill).

Solution to Problem

An electronic endoscope processor according to an embodiment of the present disclosure includes: a converting means for converting each piece of pixel data that is made up of n (n≥3) types of color components and constitutes a color image of a biological tissue in a body cavity into a piece of pixel data that is made up of m (m≥2) types of color components, m being smaller than n; an evaluation value calculating means for calculating, in units of pixels, an evaluation value related to a target illness based on the converted pieces of pixel data that are made up of m types of color components; and a lesion index calculating means for calculating a lesion index for each of a plurality of types of lesions related to the target illness based on the evaluation values calculated for the pixels.

According to an embodiment of the present disclosure, it is preferable that the lesion index calculating means calculates a sum of the plurality of types of lesion indices as an overall lesion index.

According to an embodiment of the present disclosure, it is preferable that the lesion index calculating means calculates a first lesion index based on the number of pixels for which the evaluation value calculated by the evaluation value calculating means is in a first range, and calculates a second lesion index based on the number of pixels for which the evaluation value is in a second range.

Also, according to an embodiment of the present disclosure, it is preferable that the electronic endoscope processor further includes:

an effective pixel determining means for determining, for each pixel of the color image, whether or not the pixel is an effective pixel in accordance with whether or not a pixel value satisfies a predetermined condition. In this case, it is preferable that the evaluation value calculating means calculates the evaluation value for only the effective pixels.

Also, according to an embodiment of the present disclosure, it is preferable that the electronic endoscope processor further includes: an effective pixel counting means that calculates the number of effective pixels, which is the number of pixels determined to be effective pixels. In this case, it is preferable that for each of the types of lesions, the lesion index calculating means calculates the number of lesion pixels, which is the number of pixels that correspond to the type of lesion, based on the evaluation values of the effective pixels, and calculates, as the lesion index, a proportion of the number of lesion pixels relative to the number of effective pixels.

Also, according to an embodiment of the present disclosure, it is preferable that the electronic endoscope processor further includes a color component correcting means for using a predetermined color component correction coefficient to correct the pieces of pixel data that are made up of the m types of color components and were obtained by conversion by the converting means. In this case, it is preferable that the evaluation value calculating means is configured to, in units of pixels, calculate the evaluation value related to the target illness based on the pixel data that is made up the m types of color components and was corrected by the color component correction coefficient.

Also, according to an embodiment of the present disclosure, it is preferable that the color component correction coefficient is a predetermined correction matrix coefficient for correcting the pieces of pixel data made up of the m types of color components, for example.

Also, according to an embodiment of the present disclosure, it is preferable that the evaluation value calculating means sets a reference direction that is related to the target illness and extends from a predetermined reference point in a color space defined by the m types of color components, and, for each pixel of the color image, calculates the evaluation value related to the target illness based on an extent to which a direction from the reference point to a pixel correspondence point corresponding to the converted piece of pixel data in the color space deviates from the reference direction.

Also, according to an embodiment of the present disclosure, it is preferable that the evaluation value calculating means sets a reference axis that is related to the target illness and passes through a predetermined reference point in a color plane defined by the m types of color components, and, for each pixel of the color image, calculates the evaluation value related to the target illness based on an angle formed by the reference axis and a line segment that connects the reference point and a pixel correspondence point corresponding to the converted piece of pixel data.

Also, according to an embodiment of the present disclosure, it is preferable that letting the reference axis be a first reference axis, the evaluation value calculating means sets a second reference axis that is related to a healthy site not having the target illness and that passes through the reference point in the color plane, and the evaluation value calculating means normalizes the angle θ with use of an intersecting angle of the first reference axis and the second reference axis as a maximum angle before calculating the evaluation value.

Also, according to an embodiment of the present disclosure, it is preferable that the converting means is configured to orthographically project, onto a color plane, the piece of pixel data for each pixel in a color space defined by the n types of color components.

Also, according to an embodiment of the present disclosure, it is preferable that the reference axis is an axis that indicates an inflamed site having a highest symptom level of the target illness, for example.

Also, according to an embodiment of the present disclosure, it is preferable that the evaluation value is a value indicating a degree of inflammation of a mucous membrane of a biological tissue in a body cavity. In this case, an ulcer, which is a hole that exposes underlying tissue and does not have a mucous membrane, is excluded from the evaluation value. Accordingly, the evaluation value is a value that indicates the degree of disruption of the mucous membrane when the mucous membrane is present.

Also, according to an embodiment of the present disclosure, it is preferable that the m types of color components of the converted pixel data are all color components set so as to have mutually different wavelength bands.

It is preferable that the m types of color components of the converted pieces of pixel data include at least two among a red component (wavelength of 620 to 750 nm), a green component (wavelength of 495 to 570 nm), and a blue component (wavelength of 450 to 495 nm). In this case, it is preferable that the m types of color components of the converted pieces of pixel data include the red component and one out of the green component and the blue component.

Also, according to an embodiment of the present disclosure, it is preferable that the color plane is a plane that includes a red (R) component axis and a green (G) component axis, for example.

Also, according to an embodiment of the present disclosure, it is preferable that the electronic endoscope processor further includes an overlay image generating means for generating an overlay image in which colors of pixels are changed based on the evaluation values of the pixels.

Also, according to an embodiment of the present disclosure, it is preferable that the electronic endoscope processor further includes a displaying means for displaying a lesion index on a display screen of a display apparatus. It is preferable that this displaying means is configured to display a color image and an overlay image side-by-side in the same screen on the display apparatus.

Also, according to an embodiment of the present disclosure, it is preferable that the electronic endoscope processor further includes an image capturing position acquiring means for acquiring information on a position at which a color image was captured; and a report outputting means for outputting, to an output apparatus, a representation of a relationship between a plurality of positions at which color images were captured and lesion indices of the color images that were captured at the positions, with use of at least one of a table, a graph, and a schematic illustration.

Also, an electronic endoscope system according to an embodiment of the present disclosure includes: the electronic endoscope processor according to any of the above; an electronic endoscope configured to generate data expressing the color image and output the data to the electronic endoscope processor; and a display apparatus configured to display a lesion index obtained by the electronic endoscope processor.

Also, according to an embodiment of the present disclosure, it is preferable that the display apparatus is configured to display the lesion indices for the plurality of types of lesions along with the color image.

Also, according to an embodiment of the present disclosure, it is preferable that hue and saturation are excluded from the color components.

Advantageous Effects of Disclosure

According to the electronic endoscope processor and the electronic endoscope system described above, it is possible to easily make an accurate distinction between a lesion site and a normal site.

DESCRIPTION OF EMBODIMENTS

Hereinafter, embodiments of the present disclosure will be described with reference to the drawings. The following description is given taking the example of an electronic endoscope system as an embodiment of the present disclosure.

Figure 1:
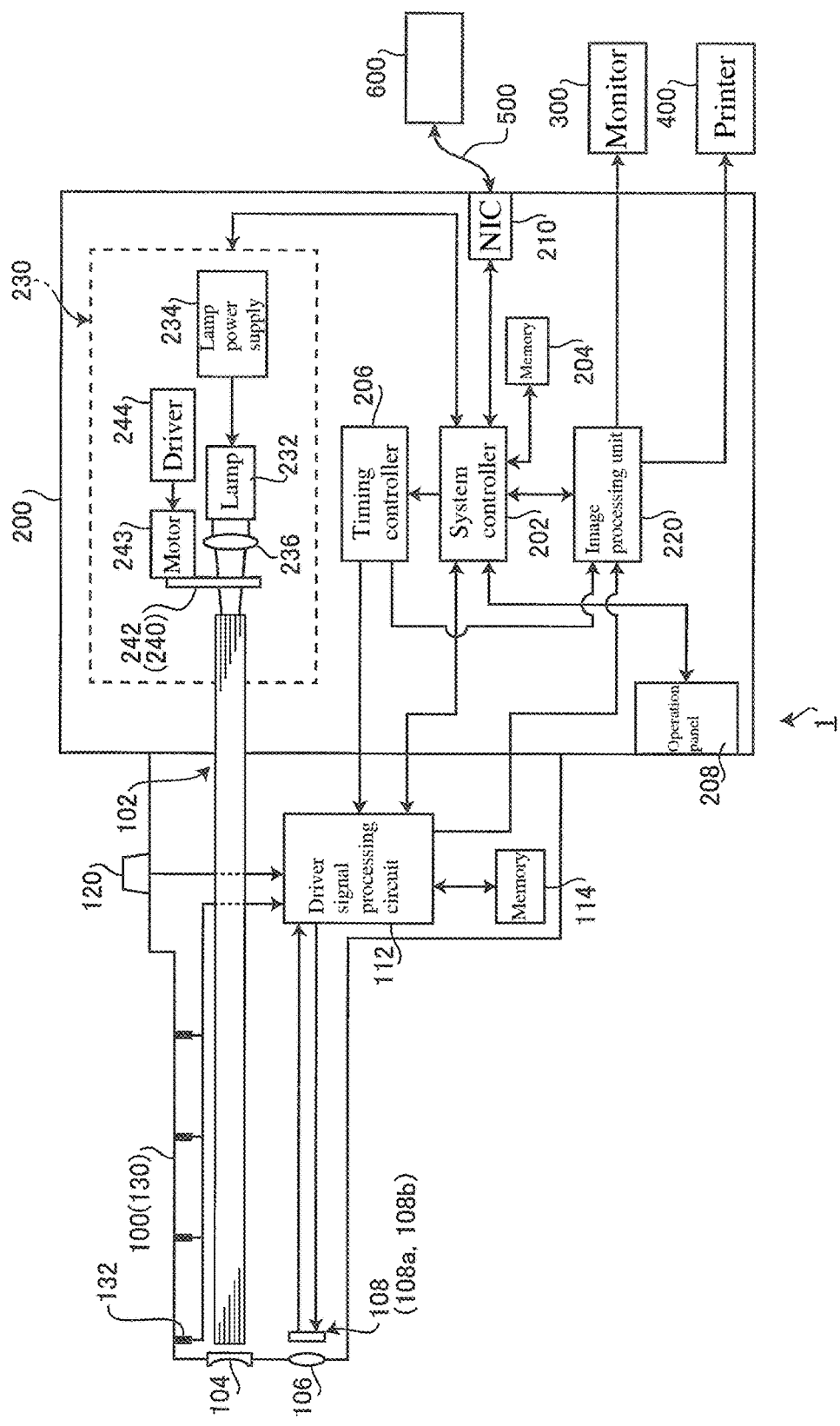
FIG. 1 is a block diagram showing a schematic configuration of an electronic endoscope system according to an embodiment of the present disclosure.

FIG. 1 is a block diagram showing the schematic configuration of an electronic endoscope system 1 according to an embodiment of the present disclosure. As shown in FIG. 1, the electronic endoscope system 1 of the present embodiment includes an electronic endoscope 100, an electronic endoscope processor 200, a monitor 300, and a printer 400.

The electronic endoscope processor 200 includes a system controller 202 and a timing controller 206. The system controller 202 executes various programs that are stored in a memory 204, and performs overall control of the electronic endoscope system 1. The system controller 202 also changes various settings in the electronic endoscope system 1 in accordance with instructions that are input to an operation panel 208 by a user (operator or assistant). The timing controller 206 outputs, to various circuits in the electronic endoscope system 1, clock pulses for adjusting the timing of operations of various units.

The electronic endoscope processor 200 also includes a light source apparatus 230 that supplies illumination light, which is white light, to an LCB (Light Carrying Bundle) 102 of the electronic endoscope 100. The light source apparatus 230 includes a lamp 232, a lamp power supply 234, a condensing lens 236, and a light adjusting apparatus 240. The lamp 232 is a high-intensity lamp that receives a supply of drive power from the lamp power supply 234 and emits illumination light, and is a xenon lamp, a metal halide lamp, a mercury lamp, or a halogen lamp, for example. The illumination light emitted by the lamp 232 is condensed by the condensing lens 236, and then guided to the LCB 102 via the light adjusting apparatus 240.

Note that the lamp 232 may be replaced with a semiconductor light emitting element such as an LD (Laser Diode) or an LED (Light Emitting Diode). A semiconductor light emitting element has features such as having a lower power consumption and smaller heat emission amount than other light sources, and therefore has an advantage of making it possible to acquire bright images while also suppressing power consumption and the heat emission amount. The ability to acquire bright images leads to an improvement in the precision of a later-described evaluation value related to inflammation. The semiconductor light emitting element is not limited to being provided in the processor 200, and may be provided in the electronic endoscope 100. For example, the semiconductor light emitting element may be provided in the distal end portion of the electronic endoscope 100.

The light adjusting apparatus 240 is an apparatus that adjusts the amount of illumination light that is guided to the LCB 102, under control of the system controller 202, and includes a diaphragm 242, a motor 243, and a driver 244. The driver 244 generates drive current for driving the motor 243, and supplies the drive current to the motor 243. The diaphragm 242 is driven by the motor 243, and changes the size of an opening for the passage of the illumination light so as to adjust the amount of illumination light that passes through the opening.

The illumination light is introduced to the LCB 102 through the entrance end thereof, propagates inside the LCB 102, is emitted from the exit end of the LCB 102, which is arranged at the distal end of the electronic endoscope 100, and irradiates a subject via a light distribution lens 104. Reflected light returning from the subject passes through an objective lens 106 and forms an optical image on the light receiving surface of a solid-state image sensor 108.

The solid-state image sensor 108 is a single-plate color CCD (Charge-Coupled Device) image sensor that has various filters, such as an IR (Infra Red) cut filter 108a and a Bayer color filter 108b, arranged on the light receiving surface, and generates three primary color R, G, and B captured image signals in accordance with the optical image that is formed on the light receiving surface. In a driver signal processing circuit 112 provided in a connection portion of the electronic endoscope 100, the generated captured image signals are amplified, then converted into image signals made up of a luminance signal Y and color difference signals Cb and Cr and further converted into digital signals, and then sent to an image processing unit 220 of the electronic endoscope processor 200. The driver signal processing circuit 112 also accesses a memory 114 and reads out unique information regarding the electronic endoscope 100. The unique information regarding the electronic endoscope 100 recorded in the memory 114 includes, for example, the pixel count, sensitivity, and operable frame rate of the solid-state image sensor 108. The unique information read out from the memory 114 is output by the driver signal processing circuit 112 to the system controller 202.

A primary color (RGB) filter has better color development characteristics than a complementary color filter. For this reason, if an RGB-format image signal obtained by an image sensor that has a primary color filter is used to calculate a later-described evaluation value related to inflammation, it is possible to improve the precision of that evaluation. Also, using a primary color filter eliminates the need to perform signal conversion in the processing for calculating the inflammation-related evaluation value. This therefore makes it possible to suppress the processing load in evaluation calculation.

The system controller 202 generates control signals by performing various arithmetic operations based on the unique information regarding the electronic endoscope 100. The system controller 202 uses the generated control signals to control the operations of and the timing of various circuits in the electronic endoscope processor 200 so as to perform processing suited to the electronic endoscope 100 that is connected to the electronic endoscope processor 200.

The timing controller 206 supplies a clock pulse to the driver signal processing circuit 112 and the image processing unit 220 in accordance with timing control performed by the system controller 202. In accordance with the clock pulse supplied from the timing controller 206, the driver signal processing circuit 112 controls the driving of the solid-state image sensor 108 according to a timing synchronized with the frame rate of the images processed by the electronic endoscope processor 200.

Under control of the system controller 202, the image processing unit 220 of the electronic endoscope processor 200 generates a video signal for displaying endoscopic images and the like on a monitor, based on an image signal received from the driver signal processing circuit 112 of the electronic endoscope 100, and outputs the video signal to a monitor 300, which is a display apparatus. The operator observes a patient's gastrointestinal tract, performs treatment, or the like while checking the endoscopic images displayed on the monitor 300. The image processing unit 220 also generates a report output signal (print signal) for printing out a later-described report screen, based on an image signal, and outputs the report output signal to the printer 400.

The electronic endoscope processor 200 is connected to a server 600 via a network interface 210 and a network 500. The electronic endoscope processor 200 acquires information related to endoscopic examination (e.g., electronic patient record information and operator information) from the server 600 and displays it on the monitor 300 or the operation panel 208, and also transmits endoscopic examination results (endoscopic image data, examination conditions, later-described image analysis results, operator findings, etc.) to the server 600 for storage therein.

The electronic endoscope system 1 also includes a function for recording multiple still endoscopic images in association with information on the image capturing location (i.e., the position (insertion length) of the distal end portion of the electronic endoscope 100 when an image was captured). Multiple light sensors 132 are provided on the outer circumferential surface of an insertion portion 130 of the electronic endoscope 100, at even intervals (e.g., 5 cm intervals) in the length direction. The light sensors 132 are light receiving elements such as photodiodes, and detect external light (indoor light in the room in which the endoscopic examination is performed). External light is not detected by the light sensors 132 that are provided in the portion of the insertion portion 130 that is inserted into the gastrointestinal tract, and external light is detected by the light sensors 132 that are provided in the portion that is not inserted into the gastrointestinal tract. Accordingly, information on the position (insertion length) of the distal end portion of the electronic endoscope 100 can be acquired by determining that the insertion length of the insertion portion 130 in the gastrointestinal tract is the distribution length of the light sensors that have not detected light. The light sensors 132 are connected to the driver signal processing circuit 112, and transmit sensor signals indicating the amount of detected light to the driver signal processing circuit 112. The driver signal processing circuit 112 calculates a position (insertion length) Pos of the distal end portion of the electronic endoscope 100 based on the sensor signals from the light sensors 132.

Also, when a user operation corresponding to still image acquisition is performed on a control body 120 of the electronic endoscope 100, an operation signal is transmitted from the control body 120 to the driver signal processing circuit 112. Upon acquiring a still image acquisition operation signal from the control body 120, the system controller 202 transmits, to the image processing unit 220, the current position information (insertion length) Pos of the distal end portion of the electronic endoscope 100 along with the still image acquisition instruction. Accordingly, in the image processing unit 220, a still image of the endoscope observation image is recorded in association with the position information Pos of the electronic endoscope 100 at the time of image capturing. The processing in which the image processing unit 220 records a still image will be described in detail later.

Figure 2:
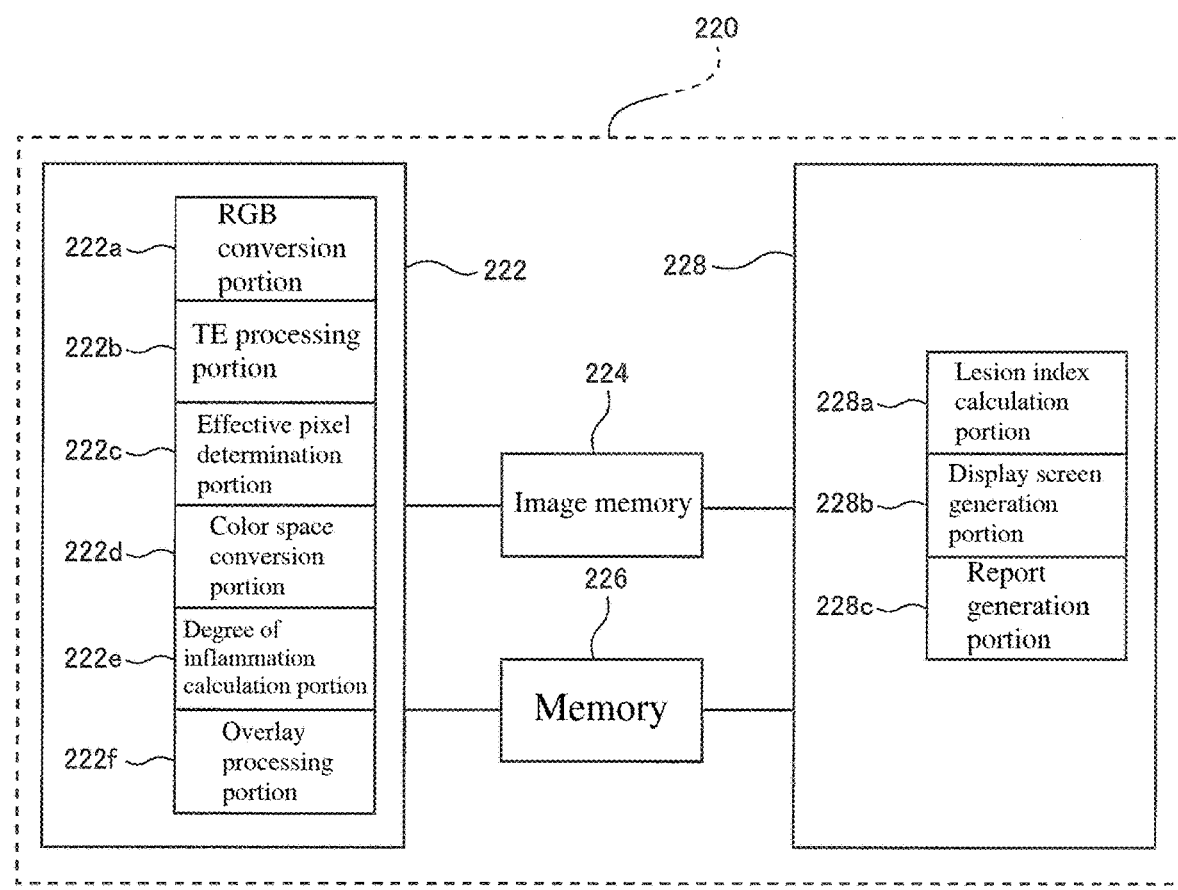
FIG. 2 is a block diagram showing a schematic configuration of an image processing unit according to an embodiment of the present disclosure.

FIG. 2 is a block diagram showing the schematic configuration of the image processing unit 220. The image processing unit 220 includes a first image processing circuit 222, an image memory 224, a memory 226, and a second image processing circuit 228. The first image processing circuit 222 performs various types of image processing on an image signal from the driver signal processing circuit 112, and outputs the resulting image signal to the image memory 224.

As shown in FIG. 2, the first image processing circuit 222, includes an RGB conversion portion 222a, a TE processing portion 222b, an effective pixel determination portion 222c, a color space conversion portion 222d, a degree of inflammation calculation portion 222e, and an overlay processing portion 222f. Also, the second image processing circuit 228 includes a lesion index calculation portion 228a, a display screen generation portion 228b, and a report generation portion 228c. Specific processing performed by these units of the first image processing circuit 222 and the second image processing circuit 228 will be described later.

Figure 3:
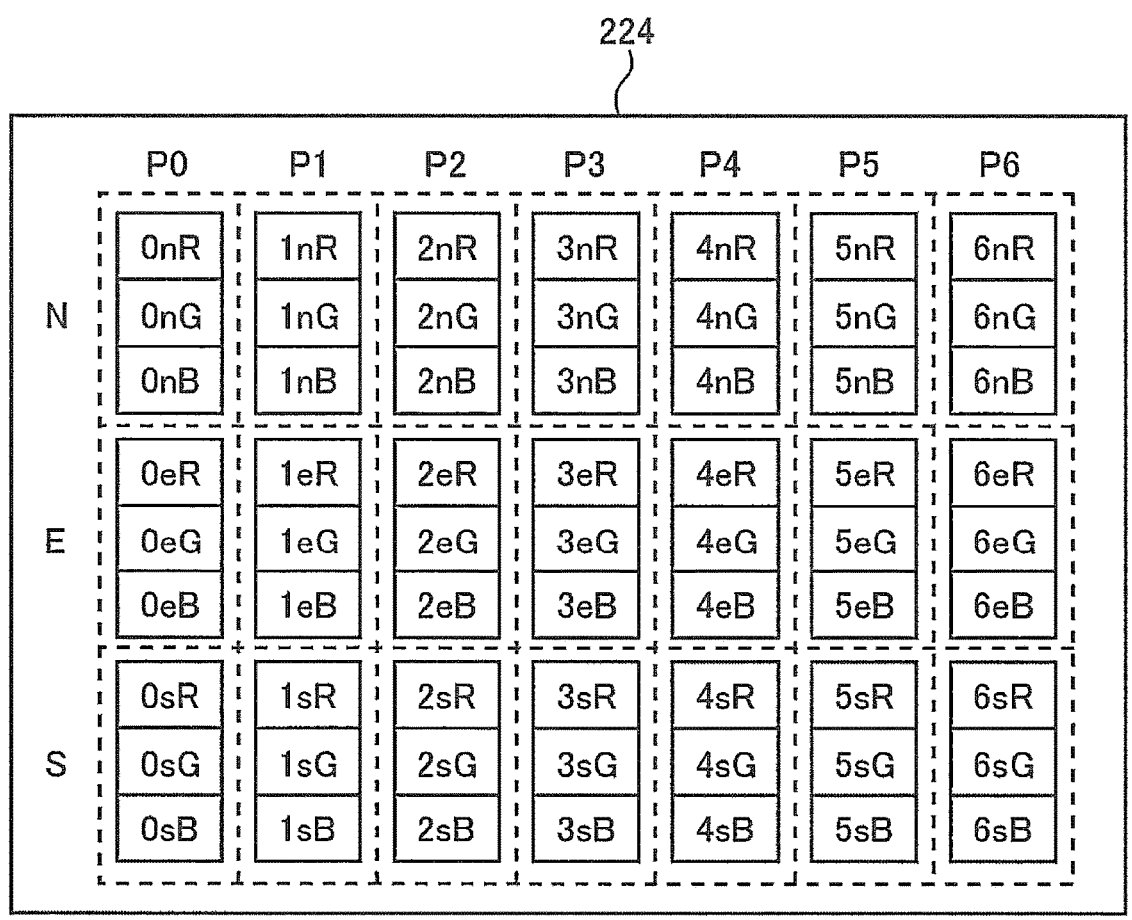
FIG. 3 is a diagram showing a schematic configuration of storage regions in an image memory 224.

FIG. 3 is a diagram showing the schematic configuration of storage regions in the image memory 224. The image memory 224 of the present embodiment is provided with seven storage region groups Pk (k=0 to 6). Each of the storage region groups Pk includes normal image memory regions knR, knG, knB (k=0 to 6) for storing three primary color signals R, G, and B that make up normal observation image data N, tone-emphasized image memory regions keR, keG, keB (k=0 to 6) for storing primary color signals R', G', B' that make up tone-emphasized image data E that is generated in later-described TE processing S3, and overlay image memory regions ksR, ksG, ksB (k=0 to 6) for storing three primary color signals R", G", B" that make up overlay image data S that is generated in later-described overlay processing S7. Specifically the image memory 224 can store up to seven data sets that each include the normal observation image data N, the tone-emphasized image data E, and the overlay image data S. The image memory 224 is configured so as to store image data output from the first image processing circuit 222 (the normal observation image data N, the tone-emphasized image data E, or the overlay image data 5) in any one of the storage region groups P0 to P6 under control of the system controller 202. Note that the storage region P0 is overwritten with image data that is successively output from the first image processing circuit 222, and always holds image data that constitutes real-time video. On the other hand, image data output from the first image processing circuit 222 is written to the storage region groups P1 to P6 only when an instruction is received from the system controller 202. In other words, the image memory 224 can record up to six still images.

Figure 4:
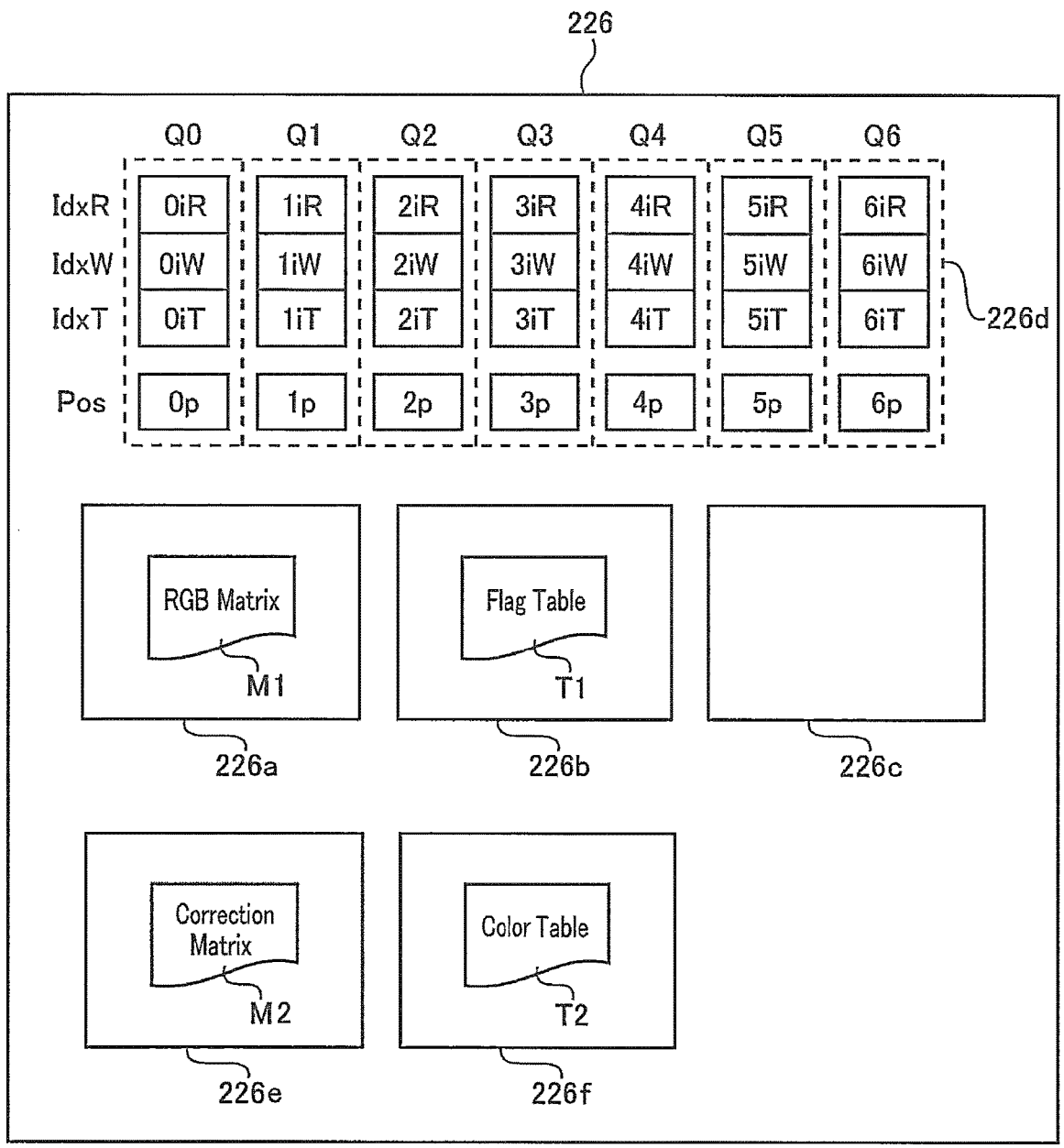
FIG. 4 is a diagram showing a schematic configuration of storage regions in a memory 226.

FIG. 4 is a diagram showing the schematic configuration of storage regions in the image memory 226. The memory 226 includes an RGB matrix storage region 226a, a flag storage region 226b, a setting information storage region 226c, a lesion index storage region group 226d, a correction matrix storage region 226e, and a color information storage region 226f. The RGB matrix storage region 226a stores an RGB conversion matrix coefficient M1 that is used in later-described RGB conversion processing S1, and the flag storage region 226b stores a flag table T1 that is used in processing performed in the first image processing circuit 222. Note that the flag table T1 is a numerical value table that is made up of flags f(x,y) that indicate analysis results regarding pixels (x,y) that make up image data. The setting information storage region 226c records various setting values that are used in processing performed in the image processing unit 220. Also, the lesion index storage region group 226d is provided with seven storage region groups Qk (k=0 to 6) that correspond to the storage region groups Pk (k=0 to 6) in the image memory 224. The storage region groups Qk each record lesion indices IdxR, IdxW, and IdxT that are analysis results regarding the image stored in the corresponding storage region group Pk.

White balance correction refers to performing color correction for only one point (e.g., white) on the achromatic color axis. Accordingly, in the case of performing evaluation on a site that has a chromatic color such as an inflamed site, if only white balance correction is performed, it is difficult to suppress variation in the evaluation value caused by individual differences in the electronic endoscope system 1 (mainly the optical components of the electronic endoscope 100). In view of this, the correction matrix storage region 226e stores a correction matrix coefficient M2 for suppressing this type of variation.

Also, the color information storage region 226f stores data that is necessary for generating an overlay image in later-described overlay processing S7.

Note that the storage region groups Pk and Qk (k=1 to 6) are associated with respective values of the position information (insertion length) Pos of the distal end portion of the electronic endoscope 100. Specifically, the storage region groups P1 and Q1 correspond to a range of insertion lengths Pos that correspond to the deepest portion in the examination range (e.g., the vicinity of the hepatic flexure of the transverse colon); the higher the k value is, the shorter the insertion length Pos is; and the storage region groups P6 and the Q6 correspond to the range of insertion lengths Pos that corresponds to the vicinity of the rectum. In other words, as still images are acquired while the insertion portion 130 of the electronic endoscope 100 is pulled from the deepest portion, the still images are recorded in the storage regions k=1 to 6 in the order of acquisition. Setting information defining the correspondence relationship between the position information Pos and the storage region groups Pk and Qk (k=1 to 6) is recorded in the setting information storage region 226c. The storage region groups Pk and Qk into which certain image data is to be recorded are determined according to the position information Pos (the position of the distal end portion of the electronic endoscope 100 at the time of capturing) of that image data.

The second image processing circuit 228 generates a monitor display video signal with use of the image signals stored in the image memory 224, and outputs the video signal to the monitor 300. The second image processing circuit 228 also generates a later-described report output signal (print signal) with use of image signals stored in the image memory 224 and lesion indices (described later) stored in the memory 226, and outputs the report output signal to the printer 400.

Figure 5:
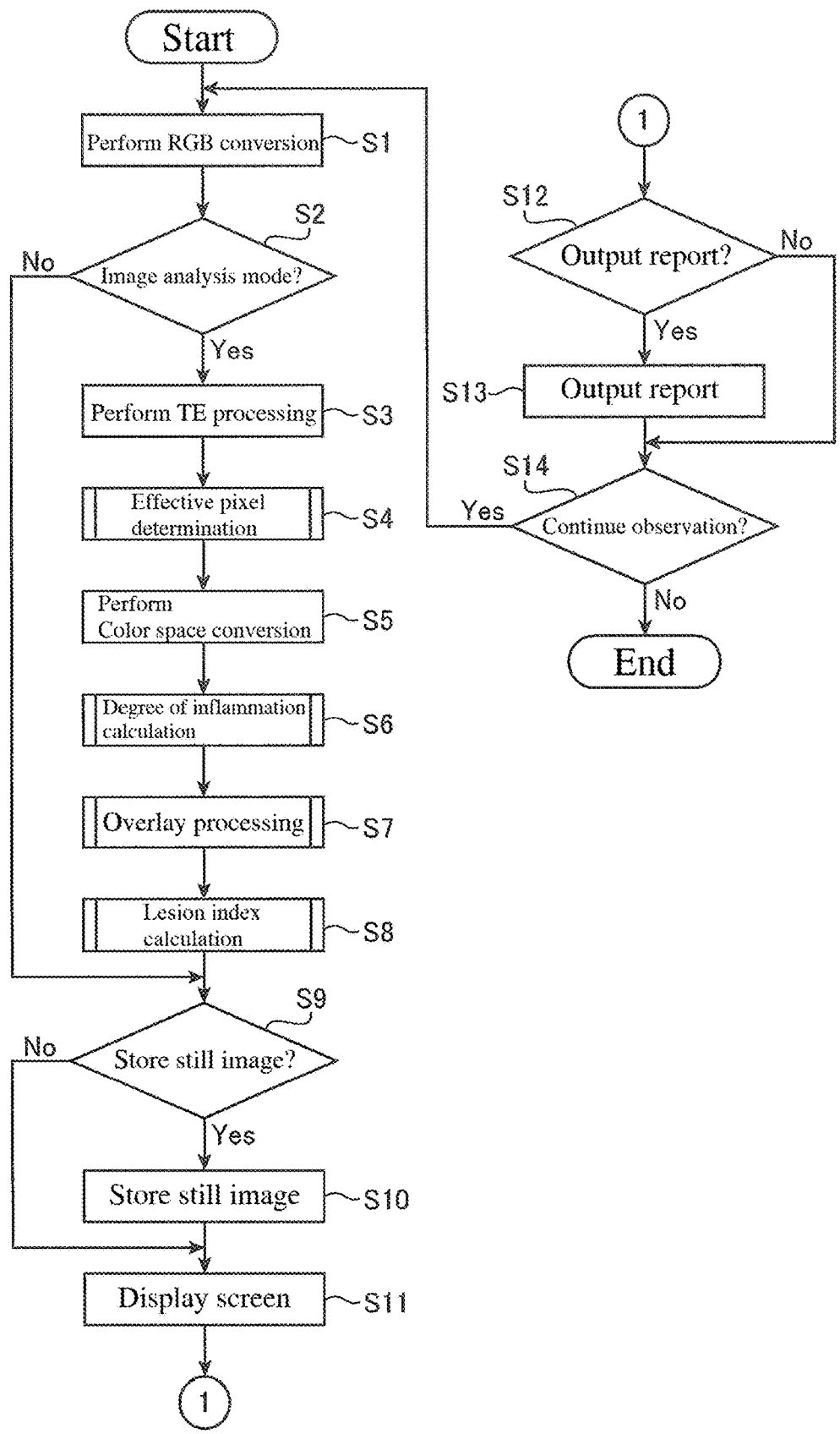
FIG. 5 is a flowchart showing a procedure of processing performed by the image processing unit.

Next, the processing performed by the image processing unit 220 will be described in detail. FIG. 5 is a flowchart showing a procedure of processing performed by the image processing unit 220. When the processing of the image processing unit 220 starts, first, RGB conversion processing S1 is performed by the RGB conversion portion 222a of the first image processing circuit 222. In the RGB conversion processing S1, the RGB conversion portion 222a amplifies a luminance signal Y and color difference signals Cb and Cr that are received from the driver signal processing circuit 112, and then converts the amplified signals into three primary color signals R, G, and B. The RGB conversion processing S1 is performed with use of the RGB conversion matrix coefficient M1 that is stored in the RGB matrix storage region 226a of the memory 226. The RGB conversion matrix coefficient M1 is set in advance in accordance with the spectral characteristics of the illumination light that is used in image capturing, and is for correcting the spectral characteristics of the illumination light while simultaneously converting the signal format from Y, Cb, Cr signals into R, G, B signals. When the RGB conversion processing S1 is complete, the three primary color signals R, G, and B that make up the generated normal observation image data N are output to the image memory 224 and respectively stored in the normal image memory regions 0nR, 0nG, and 0nB.

Next, it is determined whether or not an image analysis mode has been set (S2). The image analysis mode is an operating mode for analyzing the color components (particularly the R and G components) of pixels in image data, acquiring an evaluation result (e.g., an evaluation value or color map image regarding inflammation) regarding a target illness (lesion) based on the color component analysis result, and displaying the acquired evaluation result. The type of target illness can be selected according to the examination content. Executing the image analysis mode makes it possible to, for example, extract pixels that are in a particular color gamut in an observation image of an ulcer (a white lesion that includes white furriness or a pussy mucosal fluid) or inflammation (a red lesion that includes swelling or hemorrhaging), which are lesions in inflammatory bowel disease (IBD), for identification and display.

Note that the electronic endoscope system 1 of the present embodiment is configured to operate in two operating modes, namely the image analysis mode and a normal observation mode. The operating modes are switched by a user operation performed on the control body 120 of the electronic endoscope 100 or the operation panel 208 of the electronic endoscope processor 200. If the normal observation mode has been set (S2: No), processing moves to S9.

Figure 6:
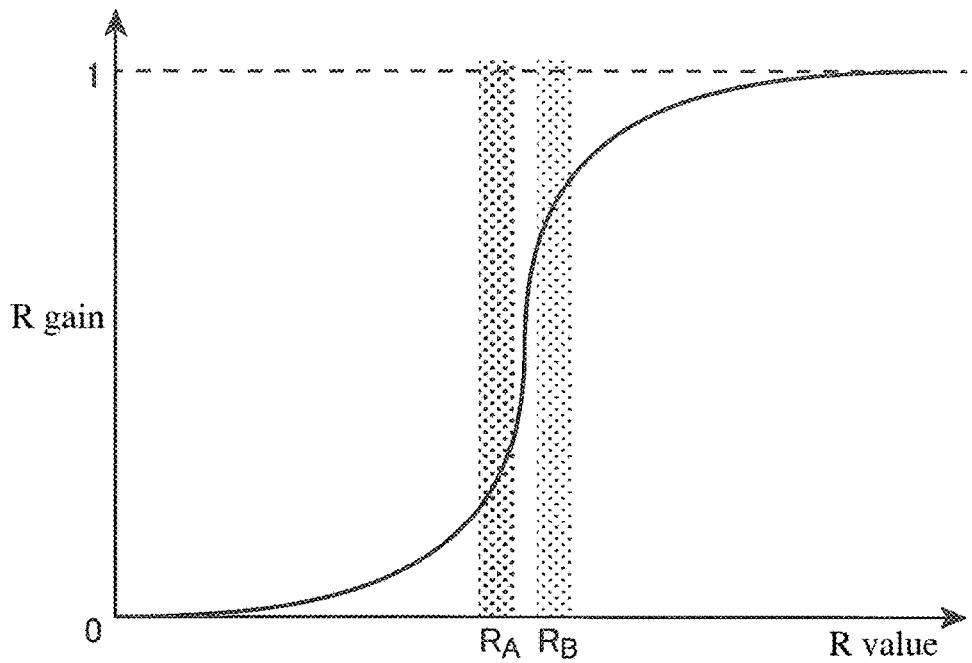
FIG. 6 shows an example of a gain curve used in TE processing.

If the image analysis mode has been set (S2: Yes), TE processing S3 is then performed by the tone emphasizing (TE) processing unit 222b. The TE processing S3 is processing for performing gain adjustment to apply nonlinear gain to the primary color signals R, G, and B, and substantially widening the dynamic range in the vicinity of color gamut (particularly the boundary portions) that is particular to the lesion that is the target of determination, so as to raise the effective resolution of color expression, in order to improve the precision in lesion determination. Specifically, in the TE processing S3, monotonically increasing nonlinear gain such as that shown in FIG. 6 is applied to the primary color signals R, G, and B so as to acquire primary color signals R', G', B' (tone-emphasized image data E). For example, letting a boundary region RA be the boundaries of the color gamut particular to an ulcer mapped to an R space, and letting a boundary region RB be the boundaries of a color gamut particular to inflammation mapped to the R space, the slope of the gain curve is steepest in the vicinity of the boundary regions RA and RB. By applying gain in accordance with this gain curve, it is possible to widen the substantial dynamic range of the primary color signal R' (the signal obtained by performing the TE processing S3 on the primary color signal R) in the vicinity of the boundary regions RA and RB, and it is possible to perform more detailed threshold value determination.

Here, different gain adjustment may be performed on the respective primary color signals R, G, and B. Furthermore, processing may be performed for applying the same nonlinear gain to the primary color signals G and B, and applying different nonlinear gain to the primary color signal R. The three primary color signals R', G', and B' (tone-emphasized image data E) generated in the TE processing S3 are then output to the image memory 224 and respectively stored in the tone-emphasized image memory regions 0eR, 0eG, and 0eB.

Note that due to the TE processing S3, inflamed sites become redder, ulcer sites become whiter, and normal sites change to a greenish hue. For this reason, when the tone-emphasized image data E generated through the TE processing S3 is displayed on the monitor 300, a lesion site (inflamed site or ulcer site) can be seen more easily than with the normal observation image data N that has not been subjected to the TE processing S3.

Figure 7:
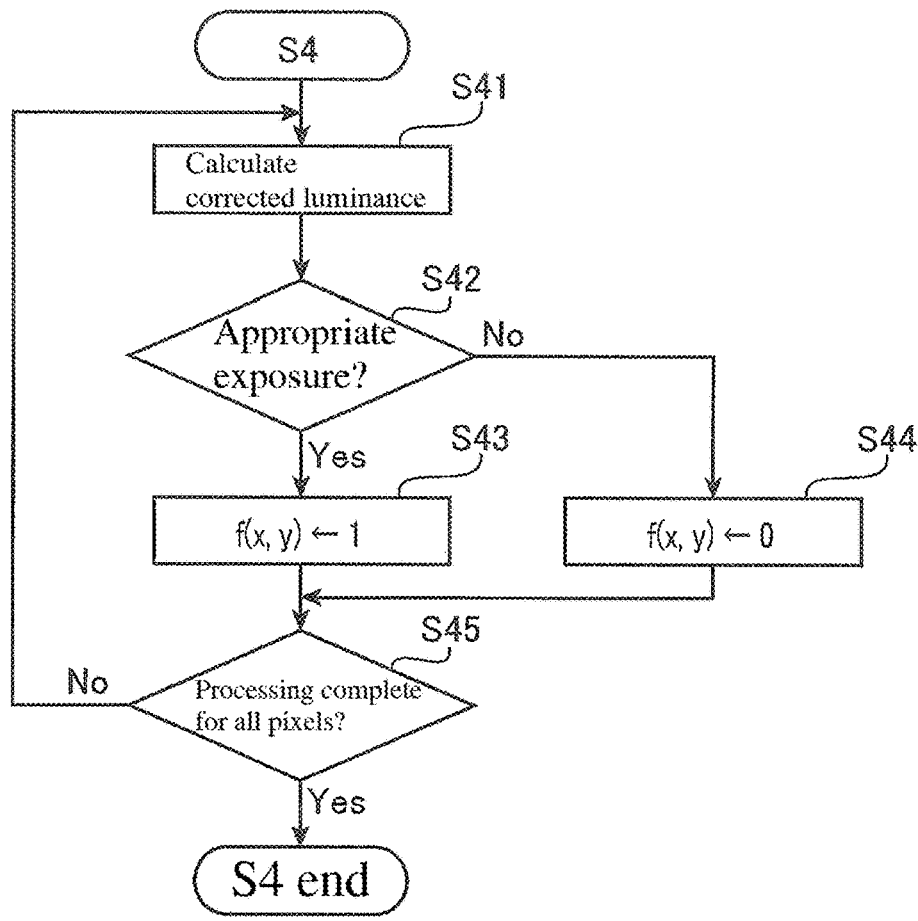
FIG. 7 is a flowchart showing a procedure of effective pixel determination processing.

When the TE processing S3 is complete, next, effective pixel determination processing S4 is performed on the tone-emphasized image data E by the effective pixel determination portion 222c. FIG. 7 is a flowchart showing a procedure of the effective pixel determination processing S4. The effective pixel determination processing S4 shown in FIG. 7 is successively performed on all of the pixels (x,y) that make up the image data. In the effective pixel determination processing S4, first, the expression shown below in Expression 1 is used to calculate a correction luminance int(x,y) for each pixel (x,y) based on the primary color signals R'(x,y), G'(x,y), and B'(x,y) (S41).

$$\text{int}(x,y)=0.3*R'(x,y)+0.59*G'(x,y)+0.11*B'(x,y) \quad \text{Expression 1}$$

Note that the calculated values of the correction luminance int(x,y) are used in appropriate exposure determination S42 that will be described later. Also, as can be understood from Expression 1, the correction luminance int(x,y) is obtained not as a simple average of the primary color signals R'(x,y), G'(x,y), and B'(x,y), but rather as a weighted average that is based on the relative visibility characteristics of humans (the operator).

Next, for each pixel, based on the correction luminance int(x,y), which was calculated in the processing S41, and the primary color signals R'(x,y), G'(x,y), and B'(x,y) of the tone-emphasized image data E, it is determined whether or not the exposure is appropriate (whether or not the exposure level is an exposure level that is necessary for image analysis) (S42). In the appropriate exposure determination S42, if at least one (or both) of the following two conditions (Expressions 2 and 3) is satisfied, it is determined that the exposure is appropriate (S42: Yes). Note that Expression 2 shown below defines an upper limit value for the correction luminance int(x,y) (overall light quantity), and Expression 3 shown below defines a lower limit value for the primary color signals R'(x,y), G'(x,y), and B'(x,y).

$$\text{int}(x,y)<235 \quad \text{Expression 2}$$

$$\text{Max}\{R'(x,y),G'(x,y),B'(x,y)\}>20 \quad \text{Expression 3}$$

For each pixel (x,y), if Expression 2 or 3 is satisfied and it is determined that the exposure level is appropriate (S42: Yes), the effective pixel determination portion 222c writes "1" as the value of the flag f(x,y) that corresponds to the pixel (x,y) in the flag table T1 that is stored in the flag storage region 226b in the memory 226 (S43). Note that the flag f(x,y) takes a flag value of either 0 or 1. These flag values are defined as follows.

0: Pixel data is ineffective
1: No lesion (normal) or lesion undetermined (pixel data is effective)

Also, in appropriate exposure determination S42, if the conditions of both Expression 2 and 3 are not satisfied, and it is determined that the exposure level is not appropriate (S42: No), the effective pixel determination portion 222c writes "0" as the value of the flag f(x,y) in the flag table T1 (S44).

Next, in processing S45, it is determined whether or not processing has been completed for all of the pixels (x,y). The above processing of S41 to S45 is repeated until processing is complete for all of the pixels (x,y).

Note that the operation of determining effective pixels, which is performed in the effective pixel determination processing S4, is performed by an effective pixel determining means. According to one embodiment, it is preferable that the effective pixel determination portion 222c shown in FIG. 2 handles the functions of the effective pixel determining means.

When the effective pixel determination processing S4 is complete, next, color space conversion processing S5 is performed by the color space conversion portion 222d. The color space conversion processing S5 is processing in which the tone-emphasized pixel data in the RGB color space, which is defined by three primary colors RGB, is converted into pixel data in an RG plane. Note that in the color space conversion processing S5, pixel data that is in the RGB color space and has not been subjected to tone emphasizing may be converted into pixel data in the RG plane.

Figure 9:
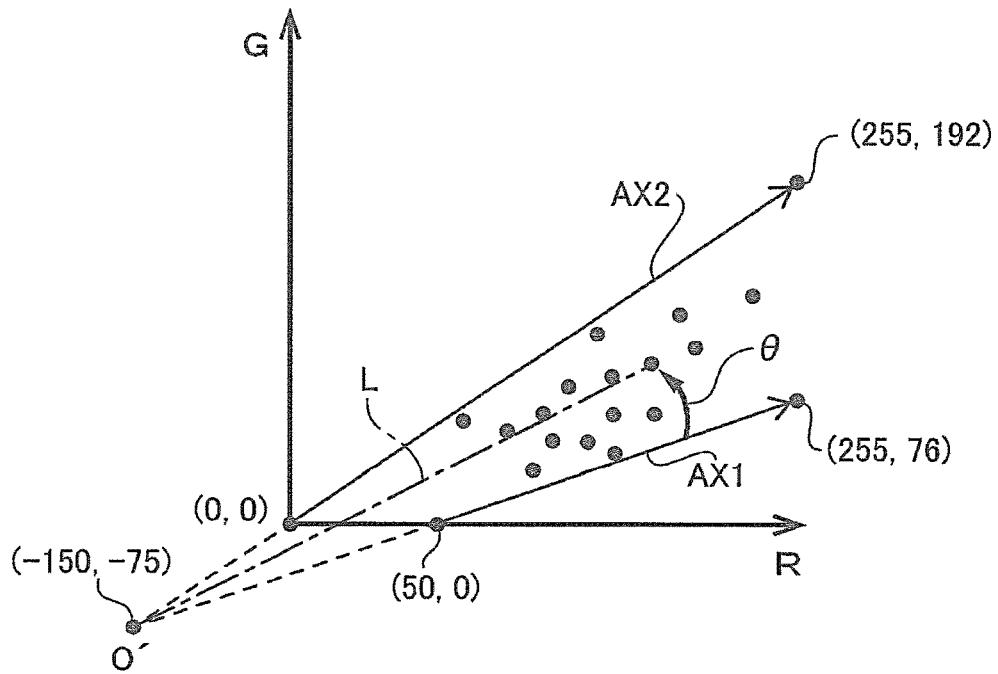
FIG. 9 is a diagram showing an RG plane on which pixel correspondence points are plotted.

FIG. 9 shows an RG plane defined by an R axis and a G axis that are orthogonal to each other. Note that the R axis is the axis for the R component (R pixel values), and the G axis is the axis for the G component (G pixel values).

In the color space conversion processing S5, for each pixel, pixel data in the RGB color space defined by the three primary colors RGB (three-dimensional pixel data constituted by three types of color component) is converted into RG pixel data (two-dimensional pixel data constituted by two types of color components). As conceptually shown in FIG. 9, the pixel data for each pixel in the RGB color space is plotted on the RG plane according to the R and G pixel values (more specifically, is plotted in a section of the RG plane that takes the values of R=0 to 255 and 0=0 to 255). Hereinafter, for the sake of convenience in the description, the points corresponding to the pixel data of pixels in the RGB color space and the points corresponding to the pixel data plotted on the RG plane will be referred to as "pixel correspondence points". Note that for the sake of clarity in FIG. 9, pixel correspondence points are shown for only some pixels rather than for all of the pixels.

Note that the color components are the components that constitute the color space (including the color plane as well). According to one embodiment, it is preferable that the color components are all set to so as to have different wavelength bands. Accordingly, in this case, hue and saturation are excluded from the concept of "color component".

In this way, in the color space conversion processing S5, pieces of pixel data in the RGB plot color space (three-dimensional data) are orthographically projected onto the RG plane, such that for each piece of pixel data, the foot of a vertical line extending from the corresponding point in the RGB color space down to the RG plane is considered to the pixel correspondence point (two-dimensional data).

Note that the operation by which the pixel data of pixels in the RGB color space is converted into pixel data in the RG plane (i.e., orthographic projection), which is performed in the color space conversion processing S5, is performed by a converting means According to one embodiment, it is preferable that the color space conversion portion 222d shown in FIG. 2 handles the functions of the converting means.

Note that if the exposure is insufficient or excessive for a pixel, the precision of the corresponding data is low, thus lowering the reliability of the analysis result. For this reason, the color space conversion processing S5 is performed on only pixels (x,y) for which the value of flag f(x,y) is set to "1", that is to say, only pixels (x,y) for which is was determined that the exposure level is appropriate in the effective pixel determination processing S4 described above.

When the color space conversion processing S5 is complete, next, degree of inflammation calculation processing S6 is performed by the degree of inflammation calculation portion 222e. The degree of inflammation calculation processing S6 is processing for calculating a degree of inflammation that indicates a target illness-related symptom level for each pixel (x,y) in the endoscopic image.

Figure 8:
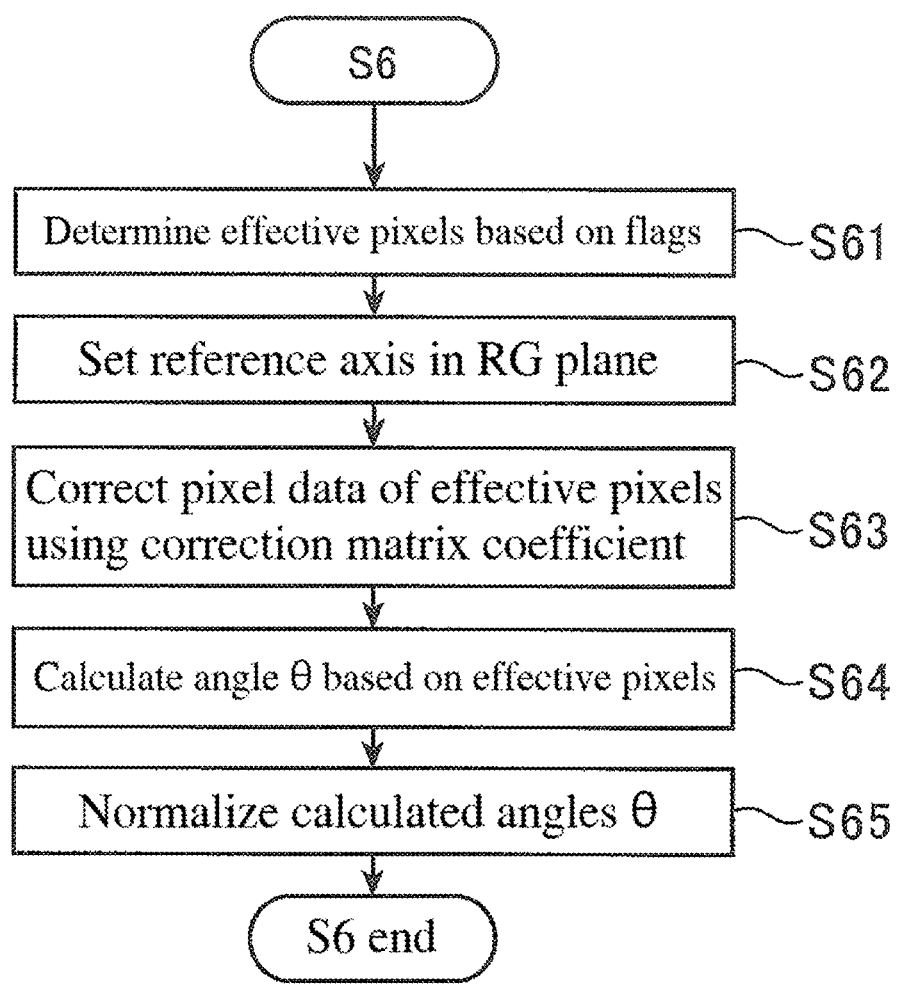
FIG. 8 is a flowchart showing a procedure of degree of inflammation calculation processing.

FIG. 8 is a flowchart showing a procedure of the degree of inflammation calculation processing S6. In the processing S61, it is determined whether or not the data for each pixel (x,y) is effective, with reference to the flag table T1. Specifically, if the value of the flag f(x,y) of a pixel is "1", it is determined that the corresponding pixel data is effective, and if the value of the flag f(x,y) of a pixel is "0", it is determined that the corresponding pixel data is ineffective.

In the degree of inflammation calculation processing S6, the processing from S62 onward is executed on only effective pixels for which the corresponding pixel data was determined to be effective in the processing S61.

Figure 10:
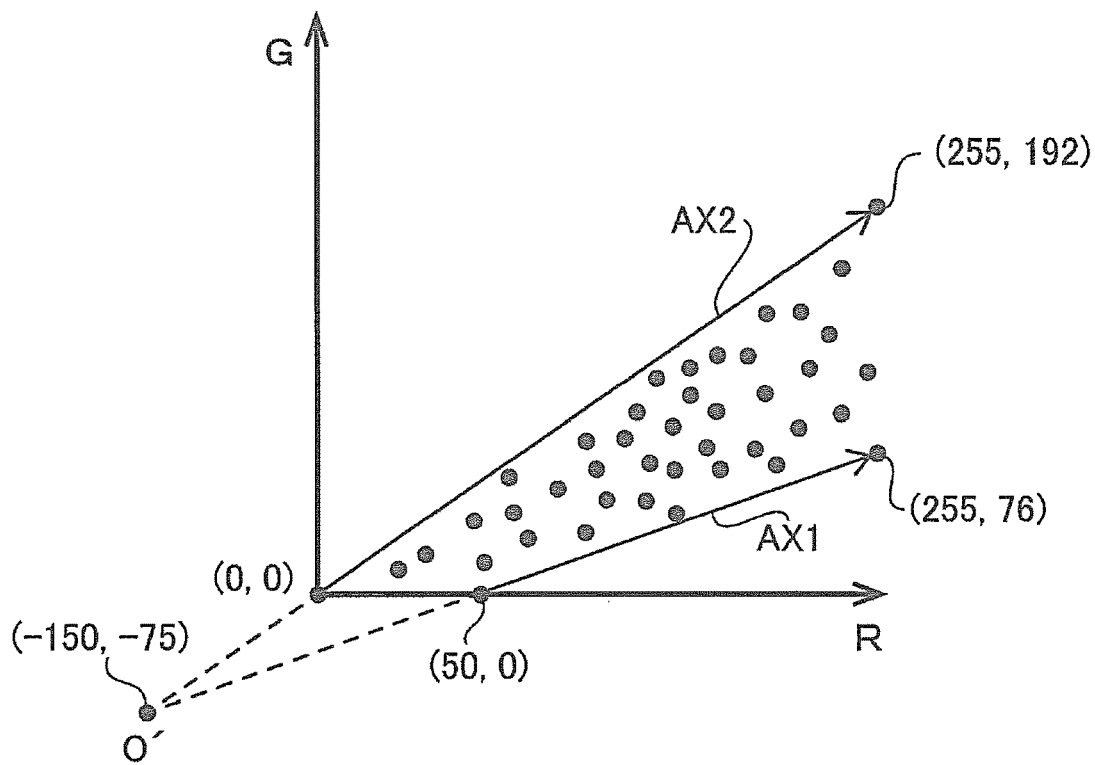
FIG. 10 is a diagram illustrating a reference axis that is set in the RG plane.

In the processing S62, a reference axis, which is necessary for calculating an evaluation value related to a target illness (e.g., a degree of inflammation that indicates the extent of inflammation), is set in the RG plane. FIG. 10 is a diagram for assisting the description of the reference axis.

Due to influences such as hemoglobin pigment, the R component is dominant over the other components (G component and B component) in the body cavity of the patient that is to be imaged, and the more intense the inflammation is, the redness (R component) typically increases relative to the other hues (G component and B component). However, in images captured inside a body cavity, the hue varies according to imaging conditions that influence brightness (e.g., degree of illumination with illumination light). For example, shaded portions not reached by the illumination light appear black (achromatic, with R, G, and B values at or near zero, for example), and portions where the illumination light strikes intensely and is specularly reflected appear white (achromatic, with R, G, and B values at or near 255, for example). In other words, even when the same inflamed abnormal site is imaged, the pixel value in the image of the abnormal site will be higher the more intensely the illumination light strikes it. For this reason, depending on the degree of illumination with the illumination light, the pixel value may take a value that has no correlation with the degree of inflammation.

Generally, normal sites inside a body cavity that are not inflamed are sufficiently covered by a mucous membrane. In contrast, abnormal sites inside a body cavity that are inflamed are not sufficiently covered by a mucous membrane. Specifically, when a blood vessel expands, blood and body fluids leak from the blood vessel, and therefore the mucous membrane becomes relatively thinner, and the color of blood becomes more easily visible. A mucous membrane is basically white in color, but has a slightly yellowish hue, and the hue (yellow hue) that appears in an image varies according to the darkness/lightness (membrane thickness). Accordingly, the darkness/lightness of the mucous membrane is also thought to be an indicator for evaluating the degree of inflammation.

In view of this, as shown in FIG. 10, a straight line that passes through (50,0) and (255,76) in the RG plane is set as one reference axis, and a straight line that passes through (0,0) and (255,192) is set as one reference axis. For the sake of convenience in the description, the former reference axis will be called the "hemoglobin variation axis AX1", and the latter reference axis will be called the "mucous membrane variation axis AX2".

The plot shown in FIG. 10 is the result of the inventor of the present disclosure analyzing a large number of sample images of body cavities. The sample images used in the analysis included examples of images of various stages of inflammation, including examples of images of inflammation of the highest symptom level (examples of images of inflammation of the most severe level) and examples of images of inflammation of the lowest symptom level (examples of images deemed to be substantially normal sites). Note that for the sake of clarity in the diagram, only a portion of the points obtained as analysis results is shown in the example in FIG. 10. The actual points obtained as analysis results are much higher in number than the number of points shown in FIG. 10.

As described above, the higher the degree of inflammation at an abnormal site is, the more intense the R component is relative to the other components (G component and B component). For this reason, an axis on the boundary line that separates regions where points are distributed and are not distributed, and that is closer to the R axis than the G axis, which is the boundary line that passes through (50,0) and (255,76) in the example in FIG. 10, is set as the axis having a high correlation with a lesion site that has the highest symptom level (an inflamed (abnormal) site with the highest symptom level). This axis is the hemoglobin variation axis AX1. Points that correspond to inflamed sites that have the highest symptom level and were imaged under various imaging conditions (e.g., degree of illumination with the illumination light) are located on the hemoglobin variation axis AX1.

On the other hand, the closer a site approximates a normal site, the more intense the G component (or the B component) is relative to the R component. For this reason, an axis on the boundary line that separates regions where points are distributed and are not distributed, and that is closer to the G axis than the R axis, which is the boundary line that passes through (0,0) and (255,192) in the example in FIG. 10, is set as the axis having a high correlation with a lesion site with the lowest symptom level (an inflamed (abnormal) site with the lowest symptom level, which is deemed to be a substantially normal (healthy) site). This axis is the mucous membrane variation axis AX2. Points that correspond to inflamed sites that have the lowest symptom level (deemed to be substantially normal sites or healthy sites) and were imaged under various imaging conditions (e.g., degree of illumination with the illumination light) are located on the mucous membrane variation axis AX2.

To give a further description, an inflamed site with the highest symptom level for a target illness is accompanied by bleeding. On the other hand, an inflamed site with the lowest symptom level is a substantially normal site, and therefore is covered by a sufficient mucous membrane. For this reason, it can be understood that the points in the RG plane shown in FIG. 10 are distributed in the region sandwiched between the axis that has the highest correlation with blood (hemoglobin pigment) and the axis that has the highest correlation with the hue of the mucous membrane. For this reason, out of the boundary lines that separate regions where points are distributed and are not distributed, the boundary line closer to the R axis (higher R component) corresponds to the axis that indicates an inflamed site with the highest symptom level (hemoglobin variation axis AX1), and the boundary line closer to the G axis (higher G component) corresponds to the axis that indicates an inflamed site with the lowest symptom level (mucous membrane variation axis AX2).

Returning to FIG. 8, in the processing S63, the pixel data (R, G) is corrected using a correction matrix coefficient. The correction matrix coefficient M2 is stored in the correction matrix storage region 226e of the memory 226. In the processing S63, in order to suppress variation in score values when the same lesion site is imaged with different electronic endoscope system (in other words, individual differences between electronic endoscopes), the pixel data (R, G) at the pixel correspondence point of each effective pixel is corrected with use of the correction matrix coefficient M2.

Example of Correction Matrix Coefficient

R and G are corrected to $R_{new}$ and $G_{new}$ with use of the correction matrix coefficients $M_{00}$-$M_{11}$.

$R_{new}$: corrected pixel data (R component)
$G_{new}$: corrected pixel data (G component)
$M_{00}$-$M_{11}$: correction matrix coefficient
R: uncorrected pixel data (R component)
G: uncorrected pixel data (G component)

Note that the operation of correcting the pixel correspondence point of each effective pixel with use of the correction matrix coefficient M2, which is executed in this processing S63, is performed by a color component correcting means. According to one embodiment, it is preferable that a color correction circuit in the image processing unit 220 shown in FIG. 2 handles this function.

In the processing S64, an angle for calculating a degree of inflammation is calculated for the pixel data ($R_{new}$, $G_{new}$) of each effective pixel that is obtained by the correction performed with use of the correction matrix coefficient M2. Specifically, the processing S64 is processing for calculating, for each effective pixel, an angle θ formed by the hemoglobin variation axis AX1 and a line segment L that connects the pixel correspondence point ($R_{new}$, $G_{new}$) and an intersection (reference point) O' of the hemoglobin variation axis AX1 and the mucous membrane variation axis AX2 (see FIG. 9). Note that the reference point O' is located at the coordinates (−150,−75).

When the brightness of the captured image of a body cavity changes according to the degree of illumination with the illumination light, the hue of the captured image is influenced by individual differences, the imaged location, the state of inflammation, and the like, but in the RG plane, the hue changes approximately along the hemoglobin variation axis AX1 at an inflamed site with the highest symptom level, and the hue changes approximately along the mucous membrane variation axis AX2 at an inflamed site with the lowest symptom level, that is to say a healthy site with substantially no illness. It is also inferred that the hue of the captured image at an inflamed site with a moderate symptom level also changes with the same tendency. Specifically, when a pixel correspondence point corresponding to an inflamed site changes according to the degree of illumination with the illumination light, a shift occurs in the azimuth angle direction with the reference point O' serving as the origin. In other words, when a pixel correspondence point corresponding to an inflamed site changes according to the degree of illumination with the illumination light, the distance from the reference point O' changes while the angle θ remains constant. This means that the angle θ is a parameter that is substantially not influenced by change in the brightness of the captured image.

The lower the angle θ is, the more intense the R component is relative to the G component, which indicates that the symptom level of the inflamed site is higher. Also, the higher the angle θ is, the more intense the G component is relative to the R component, which indicates that the symptom level of the inflamed site is lower.

In view of this, in the processing S65, for each of the effective pixels, the angle θ is normalized so as to take a value of 255 when the angle θ is zero and take a value of zero when the angle θ is $θ_{MAX}$. Note that $θ_{MAX}$ is equivalent to the angle formed by the hemoglobin variation axis AX1 and the mucous membrane variation axis AX2. Accordingly, a degree of inflammation that falls within the range of 0 to 255 (8-bit information) is calculated for all of the effective pixels.

In this way, a reference direction related to a target illness, such as the axis direction of the hemoglobin variation axis AX1 or the mucous membrane variation axis AX2, is set extending from a predetermined reference point O' in a color plane (color space) defined by two types of color components, namely the R component and the G component, and, for each pixel, an evaluation value related to that target illness is calculated based on the extent to which the direction from the reference point O' in the color space to the pixel correspondence point deviates from the reference direction.

Furthermore, in the RG plane, the mucous membrane variation axis AX2 (second reference axis) related to a healthy site having no target illness is set passing through the reference point O', and the angle θ is normalized with use of the intersecting angle of the hemoglobin variation axis AX1 (first reference axis) and the mucous membrane variation axis AX2 as the maximum angle $θ_{MAX}$ before calculating the evaluation value.

Note that the operation of calculating the evaluation value related to the target illness (here, the degree of inflammation) for each effective pixel, which is executed in the processing S65, is performed by an evaluation value calculating means. According to one embodiment, it is preferable that the degree of inflammation calculation portion 222e shown in FIG. 2 handles the functions of the evaluation value calculating means.

When the degree of inflammation calculation processing S6 is complete, next, overlay processing S7 is performed by the overlay processing portion 222f. The overlay processing S7 is processing for generating primary color signals R", G", and B" that make up overlay image data S that expresses a captured image in mosaic form with use of display colors that correspond to the degrees of inflammation that were calculated in the degree of inflammation calculation processing S6.

Specifically, in order to be able to display an overlay image, a color table T2 that associates values of the degree of inflammation with predetermined display colors is stored in the color information storage region 226f of the memory 226. In the color table T2, different display colors are associated with each range of five values, for example. For example, yellow is associated with the range of degree of inflammation values 0 to 5, different display colors are associated with successive groups of five higher values according to the color order in the hue circle, and red is associated with the range of values 250 to 255.

In the overlay processing S7, based on the color table T2, the effective pixels in the normal observation image data N are converted into colors that correspond to the value of the degree of inflammation obtained in the degree of inflammation calculation processing S6, and the overlay image data S made up of pixels with the converted display colors is generated.

Note that the operation of generating the overlay image, which is executed in the overlay processing S7, is performed by an overlay image generating means According to one embodiment, it is preferable that the overlay processing portion 222f shown in FIG. 2 handles the functions of the overlay image generating means.

When the overlay processing S7 is complete, the overlay image data S generated by the overlay processing S7 is output to the image memory 224 and stored in the overlay image memory regions 0sR, 0sG, and 0sB (k=0 to 6).

Next, lesion index calculation processing S8 is performed by the lesion index calculation portion 228a of the second image processing circuit 228. The lesion index calculation processing S8 is processing for calculating the proportion (lesion index) of pixels that express sites deemed to have an illness (e.g., the pixels for which the value of the degree of inflammation calculated in the degree of inflammation calculation processing S6 is a certain value or higher) among all of the effective pixels in the endoscopic image (the pixels determined to have an appropriate exposure level in the effective pixel determination processing S4). Note that the lesion index may be a value that is calculated by another method, such as the sum value or the average value of the degree of inflammation of all of the effective pixels.

Figure 11:
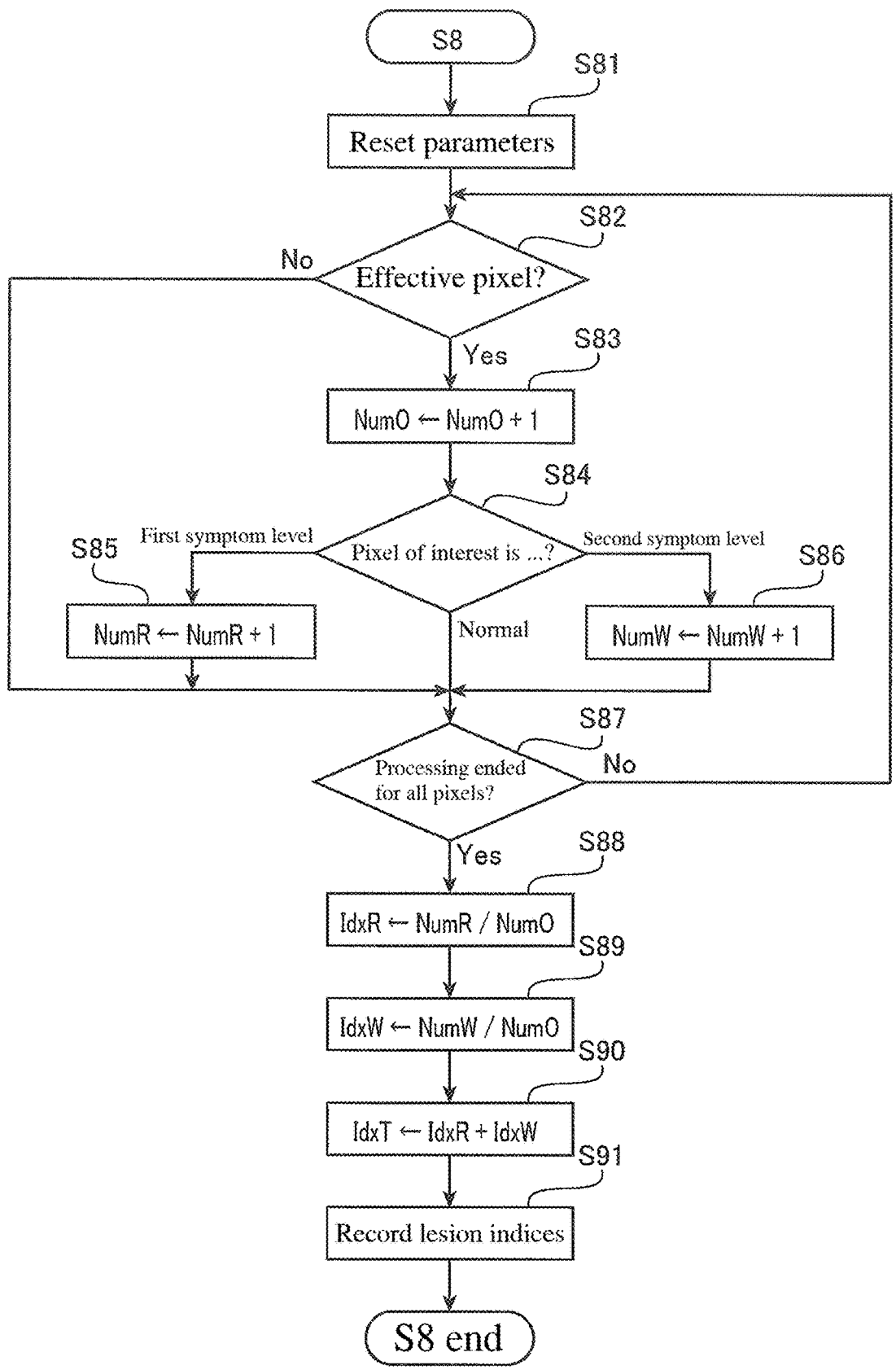
FIG. 11 is a flowchart showing a procedure of lesion index calculation processing.

FIG. 11 is a flowchart showing a procedure of the lesion index calculation processing S8. In the lesion index calculation processing S8, first, the parameters are reset (S81). Note that NumO, NumR, and NumW are counters for respectively counting the number of effective pixels, the number of pixels that express a site corresponding to a first symptom level of a target illness (e.g., the value of the degree of inflammation is greater than or equal to a first value and less than a second value), and the number of pixels that express a site corresponding to a second symptom level of the target illness (e.g., the value of the degree of inflammation is greater than or equal to the second value).

Note that the operations of counting effective pixels, which are executed in the processing S81 and also processing S82 to 87 described later, are performed by an effective pixel counting means According to one embodiment, it is preferable that the lesion index calculation portion 228a shown in FIG. 2 handles the functions of the effective pixel counting means.

Next, it is determined whether or not the pixel of interest (x,y) is an effective pixel with reference to the flag table T1 (S82). If it is not an effective pixel (S82: No), the counters are not updated, and the processing moves to S87. If it is an effective pixel (S82: Yes), the counter NumO is incremented (S83). Next, it is determined whether the pixel of interest is a pixel that corresponds to normal (e.g., the value of the degree of inflammation is less than the first value), the first symptom level, or the second symptom level (S84). If it is determined that the pixel corresponds to normal (S84: normal), the processing moves to S87. Also, if it is determined that the pixel corresponds to the first symptom level (S84: first symptom level), the counter NumR is incremented (S85), or if it is determined that the pixel corresponds to the second symptom level (S84: second symptom level), the counter NumW is incremented (S86), and then the processing moves to S87.

Next, it is determined whether or not processing is complete for all of the pixels (x,y) (S87). The above processing of S81 to S87 is repeated until processing is complete for all of the pixels (x,y).

When counting is complete for all of the pixels (x,y), next, the lesion index IdxR is calculated (S88). The lesion index IdxR is the proportion of pixels that express a site corresponding to the first symptom level among the total number of effective pixels, and is calculated using the expression IdxR=NumR/NumO.

Next, the lesion index IdxW is calculated (S89). The lesion index IdxW is the proportion of pixels that express a site corresponding to the second symptom level among the total number of effective pixels, and is calculated using the expression IdxW=NumW/NumO.

Next, the overall lesion index IdxT is calculated (S90). The overall lesion index IdxT is the proportion of pixels that express an illness (a site corresponding to the first or second symptom level) among the total number of effective pixels, and is calculated using the expression IdxT=IdxR+IdxW.

Note that the operations of calculating the lesion indices and the overall lesion index, which are executed in the lesion index calculation processing S8, are performed by a lesion index calculating means According to one embodiment, it is preferable that the lesion index calculation portion 228a shown in FIG. 2 handles the functions of the lesion index calculating means.

Here, consider the case where a method similar to the above-described method is used to calculate separate lesion indices for an inflammatory bowel disease, namely an ulcer and inflammation, and the sum of the two calculated lesion indices is obtained as the overall lesion index IdxT. Through research carried out by the inventor of the present disclosure, it was found that there is a strong correlation between the thus-calculated overall lesion index IdxT in an endoscopic image of an inflammatory bowel disease and a Mayo score that indicates the severity of an inflammatory bowel disease, and that the overall lesion index IdxT is a good indicator for making a simple determination regarding the severity of an inflammatory bowel disease.

Next, the lesion indices IdxR, IdxW, and IdxT are recorded in the memory 226 (S91), and then the lesion index calculation processing S8 ends.

Next, it is determined in S9 (FIG. 5) whether or not a still image storage instruction has been given. If the image processing unit 220 receives a still image storage instruction and the position information Pos of the distal end portion of the electronic endoscope 100 from the driver signal processing circuit 112 (S9: Yes), the normal observation image data N, the tone-emphasized image data E, and the overlay image data S stored in the storage region group P0 of the image memory 224 are copied to whichever one of the storage region group P1 to P6 corresponds to the position information Pos (S10), and then screen display processing S11 is executed. If a still image storage instruction has not been received from the driver signal processing circuit 112 (S9: No), the processing moves to the screen display processing S11 without the processing S10 being performed.

Note that the operation in which the image processing unit 220 receives the position information Pos is performed by an image capturing position acquiring means. According to one embodiment, it is preferable that a position acquisition unit (not shown) in the image processing unit 220 handles the functions of the image capturing position acquiring means.

Next, the screen display processing S11 is processing for generating display screen data for display on the monitor 300, converting the data into a video signal, and outputting the video signal, and this processing is performed by the display screen generation portion 228b of the second image processing circuit 228. The display screen generation portion 228b can generate multiple types of display screen data under control of the system controller 202.

Figure 12:
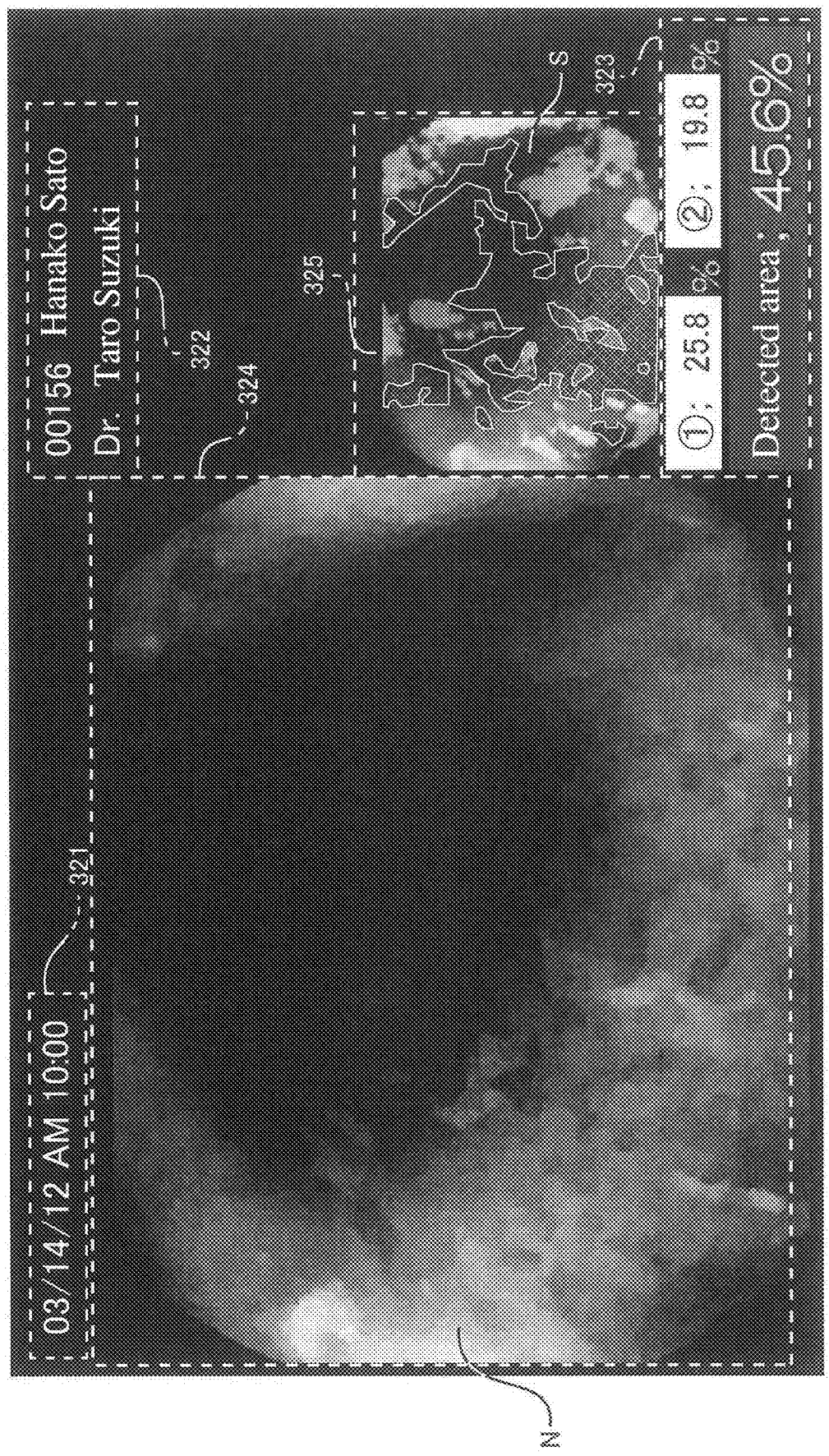
FIG. 12 shows an example of a display screen generated through screen display processing.

FIG. 12 shows an example of a display screen generated through the screen display processing S11, and more specifically shows an analysis mode observation screen 320 that is displayed during endoscopic observation in the image analysis mode. The analysis mode observation screen 320 includes a date/time display region 321 for displaying the date/time of image capturing, a basic information display region 322 for displaying examination-related basic information (e.g., carte number, patient name, and operator name), a lesion index display region 323 for displaying the lesion indices IdxR, IdxW, and IdxT that were calculated in the lesion index calculation processing S8, a normal image display region 324 for displaying the normal observation image data N (or the tone-emphasized image data E), and an analysis image display region 325 for displaying the overlay image data S (observation image resulting from the overlay processing S7).

In the screen display processing S11, the display screen generation portion 228b reads the real-time lesion indices IdxR, IdxW, and IdxT from the storage region group Q0 of the memory 226, and displays them in the lesion index display region 323. In FIG. 12, "first symptom level: 25.8%", "second symptom level: 19.8%", and "detected area: 45.6%" are respectively displays of the lesion index IdxR, the lesion index IdxW, and the overall lesion index IdxT. The display screen generation portion 228b also reads the real-time normal observation image data N (or tone-emphasized image data E) and overlay image data S from the storage region group P0 of the image memory 224, and displays them in the normal image display region 324 and the analysis image display region 325 respectively. Also, information provided by the system controller 202 is displayed in the date/time display region 321 and the basic information display region 322.

Note that the operations of displaying the lesion index IdxR, the lesion index IdxW, the overall lesion index IdxT, the normal observation image data N (or the tone-emphasized image data E) and the overlay image data S on the monitor 300, which are executed in the screen display processing S11, are performed by a displaying means. According to one embodiment, it is preferable that the display screen generation portion 228b shown in FIG. 2 handles the functions of the displaying means.

The operator performs endoscopic observation while viewing the analysis mode observation screen 320. Specifically, endoscopic observation is performed while viewing the normal observation image data N (or the tone-emphasized image data E) displayed in the normal image display region 324 and referencing the overlay image data S displayed in the analysis image display region 325. By performing particularly careful observation at sites that are colored in the overlay image data S, it is possible to perform accurate examination in which lesion sites are not overlooked. Also, by referencing the objective and specific values of the lesion indices IdxR, IdxW, and IdxT displaying in the lesion index display region 323 while performing observation, it is possible to make a more objective and detailed diagnosis without being susceptible to subjective impressions given by the normal observation image data N and the overlay image data S.

For example, in the case of inflammatory bowel diseases, as the lesion sites (inflamed sites, ulcer sites) spread and become severe, the proportion of lesion sites increases, and therefore the overall lesion index IdxT is a good indicator of severity. On the other hand, in the case of an illness with localized lesion sites (e.g., polyps), the closer the distal end portion of the electronic endoscope 100 approaches a lesion site, the wider the angle of view of the lesion site becomes, and therefore the overall lesion index IdxT increases. For this reason, the overall lesion index IdxT is a good indicator of how close the lesion site is, and by performing careful observation when the overall lesion index IdxT starts to increase, it is possible to prevent a lesion site from being overlooked.

Next, it is determined whether or not a report output instruction has been received from the system execution controller 202 (S12). When a report output execution instruction is given through a user operation performed on the control body 120 of the electronic endoscope 100 or the operation panel 208 of the electronic endoscope processor 200, the system controller 202 sends, to the image processing unit 220, an instruction to execute later-described report output processing S13. If an instruction to execute the report output processing S13 has been output from the system controller 202 (S12: Yes), the report output processing S13 is subsequently performed. Also, if such an execution instruction has not been output (S12: No), the processing moves to S14 without the report output processing S13 being performed.

Figure 13:
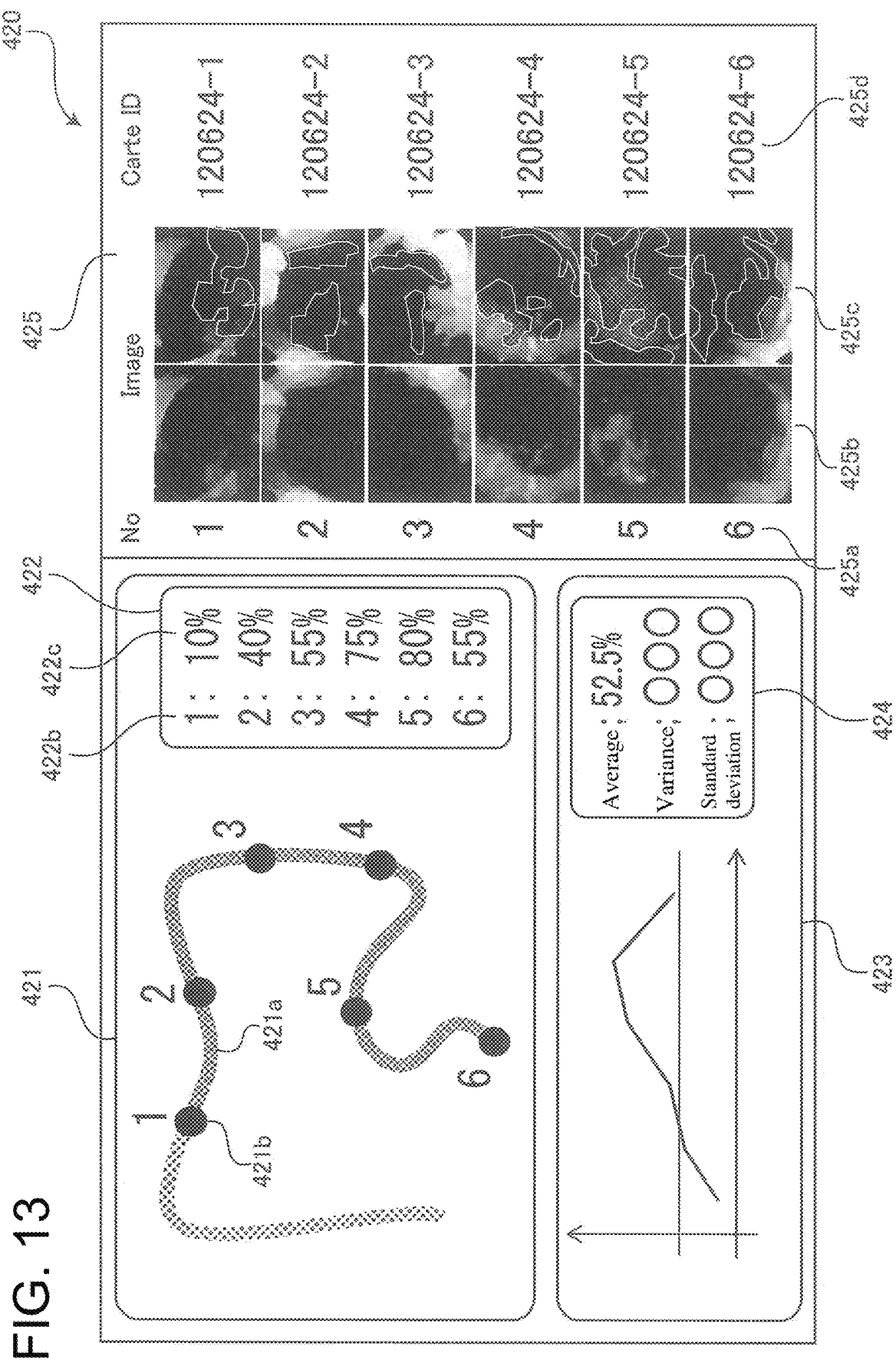
FIG. 13 shows a report screen that is printed in report output processing.

The report output processing S13 is processing for generating a report screen 420 that organizes the endoscopic examination results, converting the report screen 420 into a report output signal (print signal), outputting the report output signal to the printer 400, and printing the report screen 420. The report screen 420 shown in FIG. 13 includes a colon model diagram 421, a lesion index list 422, a lesion index distribution diagram 423, a statistical value list 424, and a thumbnail image list 425.

The colon model diagram 421 illustrates the positions at which still images were acquired (observation points), and dots 421b showing observation points 1 to 6 are arranged on a colon schematic diagram 421a. The observation points 1 to 6 respectively correspond to the storage region groups P1 to P6 in the image memory 224 and the storage region groups Q1 to Q6 in the memory 226. The lesion index list 422 shows a list of the overall lesion indices IdxT (422c) at the observation points 1 to 6 (422b). Also, the lesion index distribution diagram 423 shows a graph corresponding to the lesion index list 422. The statistical value list 424 shows a list of statistical values regarding the overall lesion index IdxT (average value, variance, and standard deviation). Also, the thumbnail image list 425 shows a list of still image thumbnail images 425b of the normal observation image data N (or tone-emphasized image data E) and still image thumbnail images 425c of the overlay image data S, which were acquired at the observation points 1 to 6 (425a), and carte numbers 425d assigned to the pieces of normal observation image data N.

Through use of the report screen 420, changes in the endoscopic image and the lesion index along the length direction of the intestinal canal can be understood at a glance, and it is possible to accurately and easily perform diagnosis and also describe the examination results to the patient.

Note that the operation of outputting the report output signal to the printer 400, which is executed in the report output processing S13, is performed by a report outputting means. According to one embodiment, it is preferable that the report generation portion 228c shown in FIG. 2 handles the functions of the report outputting means.

Next, it is determined whether or not endoscopic observation is to be continued (S14). The above-described processing S1 to S14 is repeated until a user operation for instructing the ending of endoscopic observation or the stopping of operation of the electronic endoscope system 1 is performed on the operation panel 208 of the electronic endoscope processor 200 (S14: No).

As described above, according to this embodiment, the sum of multiple types of lesion indices is calculated as the overall lesion index, thus making it possible to make an overall evaluation of the symptom level of the subject in the captured images. Also, the first lesion index is calculated based on the number of pixels for which the evaluation value is within the first range, and the second lesion index is calculated based on the number of pixels for which the evaluation value is within the second range, thus making it possible to make a detailed evaluation of the size of the region occupied by a lesion site for each symptom level. For this reason, if the same lesion site is observed after several days, it is possible to find out a change over time in the size of the region occupied by the lesion site for each symptom level, thus making it possible to precisely find out the extent of progression of the lesion site.

Also, as described above, according to this embodiment, the effective pixels are pixels that satisfy predetermined conditional expressions, and an evaluation value is calculated only for the effective pixels, thus making it possible to reduce the processing load in evaluation value calculation, as well as obtain precise evaluation values. At this time, for each type of lesion, the number of lesion pixels, which is the number of pixels corresponding to a type of lesion, is calculated based on the evaluation values of the effective pixels, and the proportion of the number of lesion pixels relative to the number of effective pixels is set as the lesion index, thus making it possible to find out the proportion of each lesion among the effective pixels in a captured image, and making it possible to find out the symptom level of each lesion site and expansion of the lesion site at the same time.

Also, as described above, according to this embodiment, in addition to the hemoglobin variation axis AX1 (the first reference axis), the mucous membrane variation axis AX2 (second reference axis) that passes through the reference point O' and is related to a healthy site not having the target illness is set in the color plane, and the angle θ is normalized with use of the intersecting angle of the hemoglobin variation axis AX1 and the mucous membrane variation axis AX2 as the maximum angle $\theta_{MAX}$ before calculating the evaluation value, thus making it possible to easily categorize the degrees of the symptom levels of the pixels according to the magnitudes of the evaluation values from 0 to 1.

Note that as described above, according to this embodiment, it is preferable that the two types of color components resulting from the conversion in the color space conversion processing S5 are color components set so as to have mutually different wavelength bands. This therefore excludes a combination of hue and saturation that are not set so as to have mutually different wavelength bands. In the case of color components set with different wavelength bands, regardless of light/dark in an image, the angle θ shown in FIG. 9 does not change very much, and only the distance from the reference point O' changes. For this reason, it is preferable that color components set with wavelength bands are used as the two types of color components resulting from conversion. It is preferable that these color components include at least two among the R component, the G component, and the B component. Furthermore, it is preferable that these color components include the R component and one out of the G component and the B component. Even if the two types of color components are the R component and the B component, in the color space constituted by the R component and the B component, it is possible to calculate an evaluation value related to a target illness with use of the angle θ relative to a reference axis as shown in FIG. 9.

Also, it is preferable that the evaluation value is a value that indicates the degree of inflammation of a mucous membrane of a biological tissue. The degree of inflammation of a mucous membrane can be set finely with use of the evaluation value. In this embodiment, the symptom level is divided into two levels, but it is also possible to divide the symptom level into three or more levels and determine a lesion index for each of them.

The electronic endoscope system according to the present embodiment achieves effects and problem solutions such as the following in the applicable technical fields.

First, the electronic endoscope system according to the embodiment is a diagnostic aid for early discovery of an inflammatory illness.

Second, according to the configuration of the embodiment, it is possible to display a screen showing the extent of inflammation (the degree of inflammation, the lesion index, an overlay image, or the like) or enhance the image in a region in which inflammation is occurring, such that the operator can discover mild inflammation that is difficult to view. In particular, mild inflammation is difficult to distinguish from a normal site, and therefore the effects achieved by the configuration of the embodiment regarding the evaluation of mild inflammation are remarkable.

Third, according to the configuration of the embodiment, it is possible to provide the operator with an objective evaluation value as an evaluation of the degree of inflammation, thus making it possible to reduce differences in diagnoses among operators. In particular, there is a large advantage of being able to provide an operator having little experience with an objective evaluation value obtained by the configuration of the embodiment.

Fourth, according to the configuration of the embodiment, the load of image processing is reduced, thus making it possible to perform real-time display of images of an inflamed site. This makes it possible to improve diagnosis precision.

Fifth, according to the configuration of the embodiment, the processing load of evaluation value calculation is reduced, thus making it possible to display an overlay image and a normal image side-by-side or in a composited manner without lag. For this reason, it is possible to display an overlay image without extending the inspection time, thus making it possible to avoid an increase in the burden on the patient.

The site that is to be observed in the present embodiment is a respiratory organ or the like, or a digestive organ or the like, for example. Here, "respiratory organ or the like" includes the lungs, the ears, the nose, and the throat, for example. "Digestive organ or the like" includes the large intestine, the small intestine, the stomach, the duodenum, and the uterus, for example. The electronic endoscope system according to the embodiment is thought to have even more remarkable effects when the observation target is the large intestine. The following are specific reasons for this.

The large intestine is susceptible to diseases that can be evaluated using inflammation as a reference, and the advantage of discovering inflamed sites is greater than in the case of other organs. In particular, the evaluation value (lesion index) illustrated in the embodiment is effective as an indicator of inflammatory bowel disease (IBD), which is typified by ulcerative colitis. A method of treatment has not been established for ulcerative colitis, and therefore using the electronic endoscope system having the configuration of the embodiment is very effective in making an early diagnosis and suppressing the progression of the illness.

The large intestine is a narrower and longer organ than the stomach and the like, and the obtained images have greater depth and are darker as the depth increases. According to the configuration of the embodiment, it is possible to suppress variation in the evaluation value caused by changes in the brightness in the image. Accordingly, when the electronic endoscope system according to the embodiment is applied to the observation of the large intestine, the effects of the embodiment are remarkable. In other words, the electronic endoscope system according to the embodiment is preferably a respiratory organ electronic endoscope system or a digestive organ electronic endoscope system, and is more preferably a large intestine electronic endoscope system.

Also, although mild inflammation is generally difficult to diagnose, according to the configuration of the present embodiment, by displaying the results of degree of inflammation evaluation on the screen for example, it is possible to avoid a situation in which the operator misses mild inflammation. In particular, in the case of mild inflammation, the determination criteria are not clear, and this is a factor that causes a large amount of individual differences between operators. In this regard as well, according to the configuration of the embodiment, it is possible to provide the operator with an objective evaluation value, thus making it possible to reduce variation in diagnoses caused by individual differences.

Note that the above-described configuration of the embodiment is applicable to the calculation of an evaluation value of not only the degree of inflammation, but also cancer, polyps, and various other lesions that are accompanied by a color change, and advantageous effects similar to those described above can be achieved in these other cases as well. In other words, the evaluation value of the embodiment is preferably an evaluation value for a lesion that is accompanied by a color change, and includes an evaluation value of at least any of inflammation, cancer, and polyps.

Although an embodiment is described above, the present disclosure is not limited to the configuration of the above embodiment, and various changes can be made within the technical idea described in the claims.

In the above embodiment, RGB color space pixel data is converted into RG plane pixel data, and an inflammation evaluation value related to a target illness is calculated using the R component and the G component included in the converted pixel data, but in another embodiment, a configuration is possible in which instead of the RGB color space, pixel data in another color space (a color space defined by n (n≥3) types of color components) such as the CIE 1976 L*a*b* color space, the CIE LCh color space, the CIE 1976 L*u*v* color space, the HSB color space, the sRGB color space, the CMK color space, the CMYK color space, or the CMYG color space is converted into pixel data in a lower order color space (a color space defined by m (n>m≥2) types of color components), and that pixel data is used to perform evaluation that corresponds to each color space and is related to a different target illness (stomach atrophy, large intestine tumor, or the like) from the above embodiment.

Also, although the TE processing S3 is performed in the RGB color space in the in the above embodiment, a configuration is possible in which the TE processing S3 is performed in another color space such as the HSI color after the color space conversion processing S5.

Various types of light sources can be used as the light source used in the electronic endoscope system 1. However, a mode is also possible in which the type of light source is limited depending on the observation target of the electronic endoscope system 1 or the like (e.g., a laser type is excluded as the type of light source). Here, in the correction matrix coefficient M2, the optimum value changes according to the spectral characteristics of the light source that is used. Accordingly, in the case where the processor 200 uses multiple types of light sources (or multiple types of external light sources are switched during use) for example, the memory 226 may store a correction matrix coefficient M2 for each of the types of light source. It is therefore possible to suppress variation in the evaluation results caused by the spectral characteristics of the light source that is used.

Also, in the above embodiment, the angle θ formed by the hemoglobin variation axis AX1 and a line segment L that connects the reference point O' and the pixel correspondence point of the pixel of interest is calculated, and evaluation related to a target illness is performed based on the calculated angle θ, but the present disclosure is not limited to this. For example, a configuration is possible in which the angle formed by the line segment L and the mucous membrane variation axis AX2 is calculated, and evaluation related to a target illness is performed based on this calculated angle. In this case, the lower the calculated angle is, the more intense the G component is relative to the R component, which indicates that the severity of the inflamed site is lower, and the higher the calculated angle is, the more intense the R component is relative to the G component, which indicates that the severity of the inflamed site is higher. For this reason, in the processing S65 in FIG. 8, the calculated angle is normalized so as to take a value of zero when it is zero, and take a value of 255 when it is $\theta_{MAX}$.

Also, in the above embodiment, the intersection of the hemoglobin variation axis AX1 and the mucous membrane variation axis AX2 is set as the reference point O' in order to minimize the influence that captured image brightness has on the inflammation evaluation value, but the present disclosure is not limited to this. For example, the origin (0,0) of the RG plane located on the mucous membrane variation axis AX2 may be set as the reference point O'. In this case, the minimum required reference axis is only one axis (the mucous membrane variation axis AX2), thus reducing the processing load and improving the processing speed.

Also, although the light source apparatus 230 is integrated with the electronic endoscope processor 200 in the above embodiment, the light source apparatus 230 may be provided as an apparatus that is separate from the electronic endoscope processor 200.

Also, instead of a CCD image sensor, a CMOS (Complementary Metal Oxide Semiconductor) image sensor may be used as the solid-state image sensor 108. In general, with a CMOS image sensor, the image tends to be overall darker than in the case of a CCD image sensor. Accordingly, with the configuration of the above embodiment, the advantageous effect of being able to suppress variation in the evaluation value caused by image brightness is even more remarkable in a situation where a CMOS image sensor is used as the solid-state image sensor.

In order to precisely make a diagnosis, it is preferable to obtain high-definition images. Accordingly, from the viewpoint of further improving diagnosis precision, the image resolution is preferably 1 million pixels or more, more preferably 2 million pixels or more, and further preferably 8 million pixels or more. The higher the resolution of the image is, the greater the load becomes in processing for calculating the above-described evaluation value for all of the pixels. However, according to the configuration of the above embodiment, it is possible to suppress the processing load in evaluation value calculation, and therefore the advantageous effect of the configuration of the present embodiment is remarkable in the situation of processing a high-definition image.

Also, although the above embodiment employs a configuration for using the light sensors 132 to acquire information on the position of the distal end portion of the electronic endoscope 100 (the image capturing position), the present disclosure is not limited to this configuration, and a configuration is possible in which information on the image capturing position is acquired by another means. For example, a configuration is possible in which, instead of the light sensors 132, optical proximity sensors that each include a light source and a light receiving element are provided on the insertion portion 130 of the electronic endoscope 100. In this case, when the optical proximity sensors are inserted into the gastrointestinal tract, sensor light reflected by an inner wall of the gastrointestinal tract is detected by the light receiving elements, thus performing proximity detection. For this reason, conversely to the above embodiment, it is possible to acquire information on the position of the distal end portion of the electronic endoscope 100 by determining that the inserted length of the insertion portion 130 in the gastrointestinal tract is the distribution length of the optical proximity sensors in which light was detected by the light receiving elements.

Also, a configuration is possible in which, instead of the light sensors 132, the insertion portion 130 of the electronic endoscope 100 is provided with a movement amount sensor that detects a movement amount (movement distance and direction) by the same principle as an optical mouse. In this case, it is sufficient to provide only one movement amount sensor in the vicinity of the leading end of the insertion portion 130.

Note that the light source of the optical proximity sensor or the movement amount sensor can be a light source (e.g., an LD or an LED) that has any wavelength from near infrared light to visible light, but high-precision detection can be obtained by using a light source that emits light in the red region, which is not absorbed very much by hemoglobin and has a high reflectance with respect to the surface of biological tissue.

It is also possible to acquire magnetic resonance images, X-ray images, or ultrasonic images from outside the subject's body during endoscopic examination, and determine the position of the distal end portion of the endoscope based on such images. The position of the distal end portion of the endoscope can also be determined by calculating the movement amount of the distal end portion of the endoscope in the gastrointestinal tract by performing image analysis on endoscopic images.

Also, the determination conditions regarding the first symptom level and the second symptom level of the target illness do not overlap each other in the above embodiment, and therefore the overall lesion index is calculated as the sum of the two lesion indices. However, if the determination conditions for the respective lesions overlap each other, the overall lesion index may be obtained by dividing the number of pixels determined to have either one of the lesions by the number of effective pixels.

Also, although a still image is recorded by a manual operation performed by the operator in the above embodiment, a configuration is possible in which, while the insertion portion 130 of the electronic endoscope 100 is pulled from the deepest portion in the examination range, when the leading end of the insertion portion 130 reaches a pre-set still image acquisition position (observation point), the driver signal processing circuit 112 automatically outputs a still image storage instruction, and a still image is automatically stored.

Also, although the solid-state image sensor 108 that has the RGB Bayer color filter 108b is used in the above embodiment, it is possible to use a solid-state image sensor that has a complementary color filter with the colors Cy (cyan), Mg (magenta), Ye (yellow), and G (green).

REFERENCE SIGNS LIST

1 Electronic endoscope system
100 Electronic endoscope
132 Movement amount sensor
200 Electronic endoscope processor
202 System controller
220 Image processing unit
222 First image processing circuit
222a RGB conversion portion
222b TE processing portion
222c Effective pixel determination portion
222d Color space conversion portion
222e Degree of inflammation calculation portion
222f Overlay processing portion
224 Image memory
226 Memory
228 Second image processing circuit
228a Lesion index calculation portion
228b Display screen generation portion
228c Report generation portion
300 Monitor
400 Printer
600 Server

The invention claimed is:

1. An electronic endoscope processor comprising:
a converting means for converting each piece of pixel data that is made up of n types of color components and constitutes a color image of a biological tissue in a body cavity into a piece of pixel data that is made up of m types of color components, n being a natural number greater than or equal to 3, m being a natural number greater than or equal to 2, and m being smaller than n;
an evaluation value calculating means for calculating, in units of pixels of the color image, an evaluation value related to a target illness based on the converted pieces of pixel data that are made up of m types of color components; and
a lesion index calculating means for calculating a lesion index for each of a plurality of types of lesions related to the target illness based on evaluation values calculated for the pixels of the color image,
wherein the evaluation value calculating means is for setting a reference direction that is related to the target illness and extends from a predetermined reference point in a color space defined by the m types of color components and, for each pixel of the color image, for calculating the evaluation value related to the target illness based on an extent to which a direction from the reference point to a pixel correspondence point corresponding to the converted piece of pixel data in the color space deviates from the reference direction.

2. An electronic endoscope processor comprising:
a converting means for converting each piece of pixel data that is made up of n types of color components and constitutes a color image of a biological tissue in a body cavity into a piece of pixel data that is made up of m types of color components, n being a natural number greater than or equal to 3, m being a natural number greater than or equal to 2, and m being smaller than n;
an evaluation value calculating means for calculating, in units of pixels of the color image, an evaluation value related to a target illness based on the converted pieces of pixel data that are made up of m types of color components; and
a lesion index calculating means for calculating a lesion index for each of a plurality of types of lesions related to the target illness based on evaluation values calculated for the pixels of the color image,
wherein the evaluation value calculating means is for setting a reference axis that is related to the target illness and passes through a predetermined reference point in a color plane defined by the m types of color components and, for each pixel of the color image, for calculating the evaluation value related to the target illness based on an angle θ formed by the reference axis and a line segment that connects the reference point and a pixel correspondence point corresponding to the converted piece of pixel data.

3. The electronic endoscope processor according to claim 2,
wherein letting the reference axis be a first reference axis,
the evaluation value calculating means is for setting a second reference axis that is related to a healthy site not having the target illness and that passes through the reference point in the color plane, and
the evaluation value calculating means is for normalizing the angle θ with use of an intersecting angle of the first reference axis and the second reference axis as a maximum angle before calculating the evaluation value.

4. An electronic endoscope processor comprising:
a first image processing circuit configured to:
convert each piece of pixel data that is made up of n types of color components and constitutes a color image of a biological tissue in a body cavity into a piece of pixel data that is made up of m types of color components, n being a natural number greater than or equal to 3, m being a natural number greater than or equal to 2, and m being smaller than n, and
calculate, in units of pixels of the color image, an evaluation value related to a target illness based on the converted pieces of pixel data that are made up of m types of color components; and
a second image processing circuit configured to calculate a lesion index for each of a plurality of types of lesions related to the target illness based on evaluation values calculated for the pixels of the color image,
wherein the first image processing circuit is configured to set a reference direction that is related to the target illness and extends from a predetermined reference point in a color space defined by the m types of color components, and, for each pixel of the color image, to calculate the evaluation value related to the target illness based on an extent to which a direction from the reference point to a pixel correspondence point corresponding to the converted piece of pixel data in the color space deviates from the reference direction.

5. An electronic endoscope processor comprising:
a first image processing circuit configured to:
convert each piece of pixel data that is made up of n types of color components and constitutes a color image of a biological tissue in a body cavity into a piece of pixel data that is made up of m types of color components, n being a natural number greater than or equal to 3, m being a natural number greater than or equal to 2, and m being smaller than n, and
calculate, in units of pixels of the color image, an evaluation value related to a target illness based on the converted pieces of pixel data that are made up of m types of color components; and
a second image processing circuit configured to calculate a lesion index for each of a plurality of types of lesions related to the target illness based on evaluation values calculated for the pixels of the color image,
wherein the first image processing circuit is configured to:
set a first reference axis that is related to the target illness and passes through a predetermined reference point in a color plane defined by the m types of color components;
calculate, for each pixel of the color image, the evaluation value related to the target illness based on an angle θ formed by the reference axis and a line segment that connects the reference point and a pixel correspondence point corresponding to the converted piece of pixel data;
set a second reference axis that is related to a healthy site not having the target illness and that passes through the reference point in the color plane, and
normalize the angle θ with use of an intersecting angle of the first reference axis and the second reference axis as a maximum angle before calculating the evaluation value.

* * * * *